(12) United States Patent
Wasalathanthri et al.

(10) Patent No.: US 12,073,924 B2
(45) Date of Patent: Aug. 27, 2024

(54) MULTIVARIATE SPECTRAL ANALYSIS AND MONITORING FOR BIOMANUFACTURING

(71) Applicant: Genzyme Corporation, Cambridge, MA (US)

(72) Inventors: Dhanuka Pulasthi Wasalathanthri, Fiskdale, MA (US); Jagdish C. Tewari, Bridgewater, NJ (US); Xuezhen Kang, Bridgewater, NJ (US); Marina Hincapie, Bridgewater, NJ (US); Shawn L. Barrett, Bridgewater, NJ (US); Julie Susanne Pollock, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 17/643,128

(22) Filed: Dec. 7, 2021

(65) Prior Publication Data
US 2022/0101953 A1 Mar. 31, 2022

Related U.S. Application Data

(63) Continuation of application No. 16/290,713, filed on Mar. 1, 2019.
(Continued)

(51) Int. Cl.
*C12M 3/00* (2006.01)
*B01L 3/00* (2006.01)
(Continued)

(52) U.S. Cl.
CPC .............. *G16C 20/10* (2019.02); *C07K 1/16* (2013.01); *C12M 21/14* (2013.01); *C12M 37/00* (2013.01);
(Continued)

(58) Field of Classification Search
CPC ................................. C12M 41/48; C07K 1/16
See application file for complete search history.

(56) References Cited

U.S. PATENT DOCUMENTS 5,985,356 A    11/1999  Schultz et al.
8,304,231 B2*  11/2012  Roll .................... C12M 23/48
                                                  435/808
(Continued)

FOREIGN PATENT DOCUMENTS

CN    101074928         11/2007
CN    103630515 A        3/2014
(Continued)

OTHER PUBLICATIONS

Bro et al., "Principal component analysis," Analytical Methods, 2014, 6:2812-2831.
(Continued)

*Primary Examiner* — Nathan A Bowers
(74) *Attorney, Agent, or Firm* — Fish & Richardson P.C.

(57) ABSTRACT

The disclosure features methods that include obtaining a vibrational spectrum of a solution in a biological manufacturing system, analyzing the vibrational spectrum using a first chemometrics model to determine a value of a first quality attribute associated with the solution, analyzing the vibrational spectrum using a second chemometrics model to determine a value of a second quality attribute associated with the solution, and adjusting at least one parameter of a purification unit of the biological manufacturing system based on at least one of the values of the first and second quality attributes.

23 Claims, 21 Drawing Sheets

Related U.S. Application Data

(60) Provisional application No. 62/729,402, filed on Sep. 10, 2018, provisional application No. 62/673,845, filed on May 18, 2018, provisional application No. 62/637,891, filed on Mar. 2, 2018.

(51) Int. Cl.

| | | |
|---|---|---|
| *C07K 1/16* | (2006.01) | |
| *C12M 1/00* | (2006.01) | |
| *C12M 1/12* | (2006.01) | |
| *C12M 1/36* | (2006.01) | |
| *G01N 21/3577* | (2014.01) | |
| *G01N 21/552* | (2014.01) | |
| *G01N 30/46* | (2006.01) | |
| *G01N 30/78* | (2006.01) | |
| *G01N 30/86* | (2006.01) | |
| *G16C 20/10* | (2019.01) | |
| *B01D 15/18* | (2006.01) | |
| *G01N 21/35* | (2014.01) | |
| *G01N 21/84* | (2006.01) | |
| *G01N 30/88* | (2006.01) | |

(52) U.S. Cl.
CPC ............ *C12M 41/48* (2013.01); *C12M 47/12* (2013.01); *G01N 21/3577* (2013.01); *G01N 21/552* (2013.01); *G01N 30/46* (2013.01); *G01N 30/78* (2013.01); *G01N 30/86* (2013.01); *B01D 15/1814* (2013.01); *B01D 15/1871* (2013.01); *G01N 2021/3595* (2013.01); *G01N 2021/8416* (2013.01); *G01N 2030/8813* (2013.01); *G01N 2030/8886* (2013.01); *G01N 2201/129* (2013.01)

(56) References Cited

U.S. PATENT DOCUMENTS

| | | | |
|---|---|---|---|
| 8,502,148 | B2 | 8/2013 | Wagner et al. |
| 9,041,923 | B2 | 5/2015 | Messerchmidt |
| 10,352,770 | B2 | 11/2019 | Morales Rodriguez et al. |
| 2004/0048330 | A1* | 3/2004 | Bittner .................. C12M 41/36 382/128 |
| 2006/0043301 | A1 | 3/2006 | Mantele et al. |
| 2006/0051874 | A1* | 3/2006 | Reed ...................... G01N 21/80 436/163 |
| 2009/0296075 | A1 | 12/2009 | Hu et al. |
| 2011/0081672 | A1* | 4/2011 | Andersen ............... C12M 41/26 435/155 |
| 2014/0255994 | A1 | 9/2014 | Konstantinov et al. |
| 2014/0373606 | A1* | 12/2014 | Kraiczek .......... G01N 33/54373 156/60 |
| 2018/0113025 | A1* | 4/2018 | Morales Rodriguez ...................... G01N 21/25 |
| 2018/0339244 | A1* | 11/2018 | Hubbuch ........... G01N 30/8675 |
| 2019/0112569 | A1* | 4/2019 | Czeterko ................ C12M 41/32 |
| 2019/0272894 | A1 | 9/2019 | Wasalathanthri et al. |
| 2020/0124817 | A1* | 4/2020 | Ohmori ................ G02B 6/4471 |

FOREIGN PATENT DOCUMENTS

| | | |
|---|---|---|
| CN | 104406836 | 3/2015 |
| CN | 106715670 | 5/2017 |
| DE | 4333560 A1 | 4/1995 |
| EP | 0206433 A2 | 12/1986 |
| EP | 3173782 | 5/2017 |
| EP | 3129460 | 12/2017 |
| JP | H05322747 A | 12/1993 |
| JP | 2005-140794 | 6/2005 |
| JP | 2008-504845 | 2/2008 |
| JP | 2008-526203 | 7/2008 |
| JP | 4638153 | 2/2011 |
| JP | 2012-520078 | 9/2012 |
| JP | 2013-505462 | 2/2013 |
| TW | I553021 | 10/2016 |
| TW | 1591782 | 7/2017 |
| WO | WO 2014/137903 | 9/2014 |
| WO | WO 2015/155353 | 10/2015 |
| WO | WO 2017/088979 | 6/2017 |
| WO | WO 2017/174580 | 10/2017 |

OTHER PUBLICATIONS

Chatfield et al., "Principal component analysis," Introduction to Multivariate Analysis, Springer, 1980, 57-81.
European Office Action in Patent Application No. 19715277.0, dated Oct. 20, 2020, 4 pages.
Haenlein et al., "A Beginner's Guide to Partial Least Squares Analysis," Understanding Statistics, 2004, 3(4):283-297.
International Preliminary Report on Patentability in International Appln. No. PCT/US2019/020355, dated Sep. 8, 2020, 8 pages.
International Search Report and Written Opinion in International Appln. No. PCT/US2019/020355, dated May 24, 2019, 12 pages.
Sellin, "Partial Least Squares Analysis," International Journal of Educational Research, 1986, 10(2):189-200.
Office Action in Singapore Appln. No. 11202008436V, dated Jan. 10, 2022, 4 pages.
Office Action in European Appln No. 19715277.0, dated Jul. 5, 2022, 8 pages.
Office Action in Indian Appln. No. 202037042608, dated Aug. 11, 2022, 8 pages.
Office Action in Brazilian Appln. No. BR112020017726-1, dated Aug. 23, 2022, 5 pages (with English translation).
Office Action in Japanese Appln. No. 2020-545704, dated Nov. 22, 2022, 6 pages (with English translation).
Office Action in Russian Appln. No. 2020132277, dated Oct. 17, 2022, 19 pages (with English translation).
Office Action in Brazilian Appln. No. BR112020017726-1, dated May 18, 2023, 8 pages (with English translation).
Office Action in Chinese Appln. No. 201980028453.6, dated Jun. 24, 2023, 34 pages (with English translation).
Office Action in Singapore Appln. No. 11202008436V, dated Jun. 15, 2023, 7 pages.
Office Action in Taiwanese Appln. No. 108107091, dated Apr. 26, 2023, 43 pages (with English translation).
Office Action in Australian Appln. No. 2019226568, dated Oct. 10, 2023, 3 pages.
Office Action in Korean Appln No. 10-2020-7027993, dated Nov. 29, 2023, 11 pages.
Office Action in Chinese Appln. No. 201980028453.6, dated Nov. 29, 2023, 31 pages (with English translation).
English Translation for CN 104406836 A, Mar. 11, 2015, 6 pages.
Office Action in U.S. Appl. No. 16/290,713, dated Feb. 15, 2024, 10 pages.
Office Action in Chinese Appln. No. 201980028453.6, dated Jun. 12, 2024, 23 pages (with English translation).
Office Action in European Appln. No. 19715277.0, dated Jun. 21, 2024, 10 pages.

\* cited by examiner

| Sample | Concentration, mg/mL | | Aggregation, % | | Charge Variants | | | | | | HCP, ng/mg | |
|---|---|---|---|---|---|---|---|---|---|---|---|---|
| | | | | | Pre-Main | | Main peak | | Post-Main | | | |
| | HPLC | FT-IR | SEC | FT-IR | cIEF | FT-IR | cIEF | FT-IR | cIEF | FT-IR | Abs | FT-IR |
| U-1 | 7.10 | 7.04 | 1.20 | 1.26 | 0.14 | 0.14 | 0.76 | 0.76 | 0.09 | 0.10 | 727 | 879 |
| U-2 | 5.96 | 5.73 | 1.40 | 1.38 | 0.11 | 0.11 | 0.78 | 0.78 | 0.10 | 0.11 | 647 | 683 |
| U-3 | 5.04 | 5.10 | 1.30 | 1.27 | 0.12 | 0.11 | 0.78 | 0.79 | 0.11 | 0.10 | 948 | 934 |
| U-4 | 5.10 | 5.25 | 1.10 | 1.11 | 0.11 | 0.11 | 0.79 | 0.78 | 0.11 | 0.11 | 811 | 839 |
| U-5 | 5.94 | 5.87 | 1.30 | 1.27 | 0.10 | 0.10 | 0.83 | 0.83 | 0.07 | 0.07 | 367 | 322 |
| U-6 | 6.08 | 6.03 | 1.20 | 1.21 | N.D. | N.D. | N.D. | N.D. | N.D. | N.D. | 890 | 879 |

FIG. 17

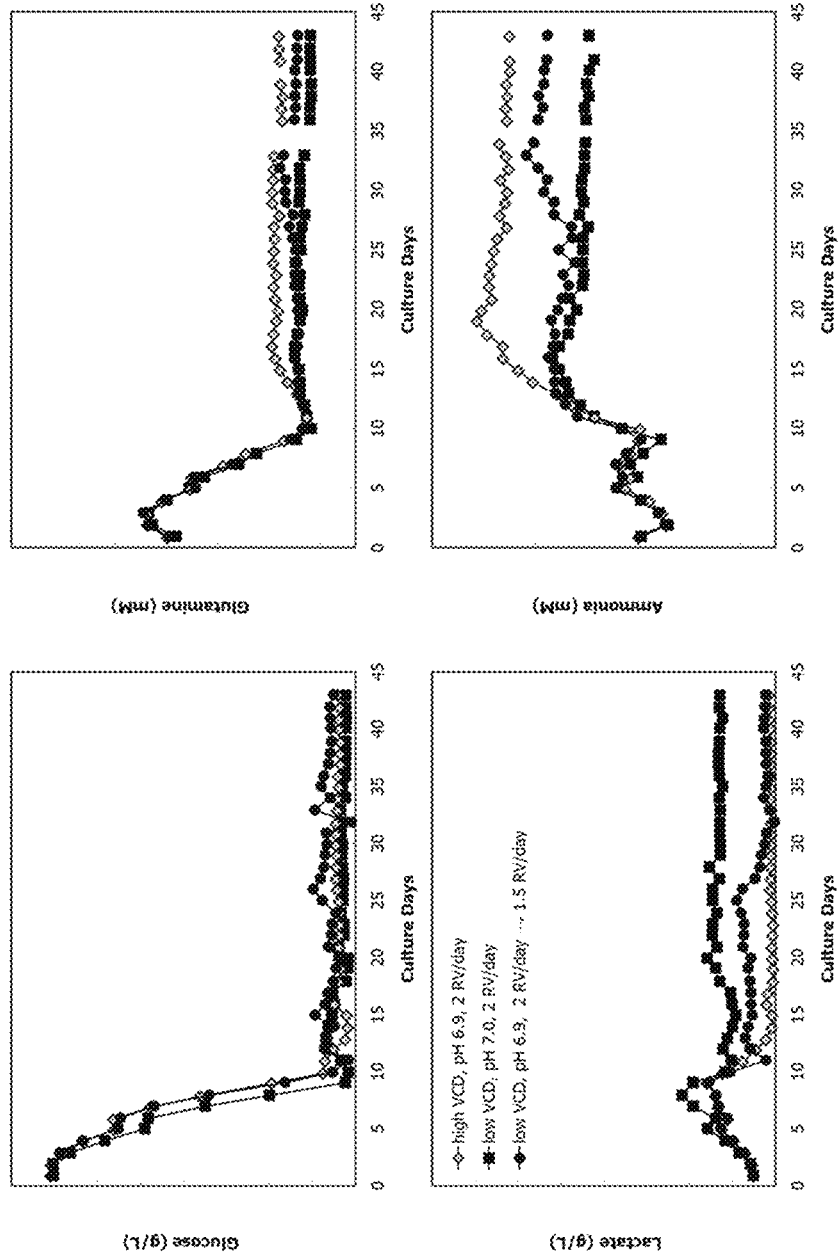

MULTIVARIATE SPECTRAL ANALYSIS AND MONITORING FOR BIOMANUFACTURING

CROSS-REFERENCE TO RELATED APPLICATIONS

This application is a continuation of U.S. patent application Ser. No. 16/290,713, filed on Mar. 1, 2019, which claims priority to the following U.S. Provisional applications, the entire contents of each of which is incorporated herein by reference: 62/637,891, filed on Mar. 2, 2018; 62/673,845, filed on May 18, 2018; and 62/729,402, filed on Sep. 10, 2018.

TECHNICAL FIELD

This disclosure relates to systems and methods for use in integrated, continuous bio-manufacturing systems.

BACKGROUND

Mammalian cells containing a nucleic acid that encodes a recombinant protein are often used to produce therapeutically or commercially important proteins. Integrated, continuous bio-manufacturing is an important aspect of reducing costs associated with therapies based on such proteins. Monitoring systems are used in bio-manufacturing to assess various biological products and process conditions.

SUMMARY

Integrated, continuous bio-manufacturing of therapeutic protein substances and other biological molecules holds tremendous promise for future production of life-saving drugs and enhancing widespread adoption of therapies that rely on the availability of such biological molecules. Two-column and multi-column chromatography systems in a variety of configurations can be used for bio-manufacturing on an industrial scale. In such systems, process monitoring of various eluent streams can be used to adjust process-related parameters and to control product attributes, for example, the selective collection of eluent streams from certain columns and the adjustment of solution buffer properties (e.g., pH).

This disclosure features methods and systems for determining solution properties such as solute concentrations, charge distribution for an analyte of interest, process and product impurities, molecular integrity, aggregation state, and pH using real-time or near real-time, sensors that are integrated in-line with chromatography systems and/or bioreactors, and coupled to an electronic controller that analyzes information measured by the sensors. Infrared spectra of the solutions can be monitored continuously, and chemometric models are used to accurately characterize quantitative chemical, physical, and/or biological properties of a variety of analytes simultaneously in solution. Spectra can be obtained in-line from flowing solutions so that measurements are performed with little or no disruption to manufacturing processes. Further, the chemometric models can extract quantitative analyte information in real time or near-real time, permitting rapid feedback and control over bio-manufacturing process-related parameters and operations.

In a first aspect, the disclosure features methods that include obtaining a vibrational spectrum of a solution in a biological manufacturing system, analyzing the vibrational spectrum using a first chemometrics model to determine a value of a first quality attribute associated with the solution, analyzing the vibrational spectrum using a second chemometrics model to determine a value of a second quality attribute associated with the solution, and adjusting at least one parameter of a purification unit of the biological manufacturing system based on at least one of the values of the first and second quality attributes.

Embodiments of the methods can include any one or more of the following features.

The methods can include using the biological manufacturing system to produce at least one of a protein-based therapeutic substance, a nucleic acid-based drug substance, and a gene therapy drug substance. The protein-based therapeutic substance can include at least one of a protein, a peptide, an antibody, and an enzyme. The nucleic acid-based drug substance can include at least one of DNA, a plasmid, an oligonucleotide, an aptamer, a DNAzyme, an RNA aptamer, an RNA decoy, a microRNA fragment, and a small interfering RNA fragment.

The first and second quality attributes can each be independently selected from the group consisting of product quality attributes, product-related impurities, and process-related impurities, for a biological product produced by the biological manufacturing system.

Obtaining the vibrational spectrum can include directing radiation to be incident on the solution and measuring attenuated totally reflected radiation from the solution. The radiation can be incident on the solution by passing through a radiation window, and the attenuated totally reflected radiation can pass through the radiation window before it is measured. The methods can include measuring the attenuated totally reflected radiation from the solution while the solution is flowing relative to the radiation window.

The radiation window can form a portion of a flow cell. The incident radiation can include infrared radiation.

The first chemometrics model can include a first set of principal vibrational components correlated with the first quality attribute. The first chemometrics model can include at least three principal vibrational components (e.g., at least five principal vibrational components). Analyzing the vibrational spectrum using the first chemometrics model can include calculating the first quality attribute value based on the first set of principal vibrational components. Calculating the first quality attribute value can include determining the value as a linear function of the first set of principal vibrational components.

The second chemometrics model can include a second set of principal vibrational components correlated with the first quality attribute. The second chemometrics model can include at least three principal vibrational components (e.g., at least five principal vibrational components). The first and second sets of principal vibrational components can have no members in common. Analyzing the vibrational spectrum using the second chemometrics model can include calculating the second quality attribute value based on the second set of principal vibrational components. Calculating the second quality attribute value can include determining the value as a linear function of the second set of principal vibrational components.

The solution can include a solution discharged from a purification unit of the biological manufacturing system. The methods can include purifying the solution in the purification unit prior to obtaining the vibrational spectrum of the solution. The purification unit can include a chromatography column.

The methods can include obtaining the vibrational spectrum by measuring radiation from the solution as the solution flows between a first purification unit and a second purification unit of the biological manufacturing system. The first and second purification units can each include a chromatography column.

The methods can include obtaining the vibrational spectrum by measuring radiation from the solution after the solution flows out of a final purification unit of the biological manufacturing system.

The solution can be a first solution, and the methods can include obtaining a vibrational spectrum of a second solution in the biological manufacturing system, analyzing the vibrational spectrum of the second solution using the first chemometrics model to determine a value of the first quality attribute for the second solution, and analyzing the vibrational spectrum of the second solution using the second chemometrics model to determine a value of the second quality attribute for the second solution. The first solution can flow between a first purification unit and a second purification unit of the biological manufacturing system, and the second solution can flow between the second purification unit and a third purification unit of the biological manufacturing system. The methods can include adjusting the at least one parameter based on at least one of the first and second quality attribute values for the first solution, and the first and second quality attribute values for the second solution.

The methods can include obtaining the vibrational spectrum and determining the first and second quality attribute values within a time period of 30 seconds or less, starting from a time at which the radiation is incident on the solution. The time period can be 10 seconds or less (e.g., 2 seconds or less).

The methods can include repeating the steps of obtaining the vibrational spectrum, analyzing the vibrational spectrum using the first chemometrics model, and analyzing the vibrational spectrum using the second chemometrics model, to determine a temporal sequence of first quality attribute values and second quality attribute values associated with successive portions of the solution. The methods can include adjusting the at least one parameter based on at least one of the temporal sequence of first quality attribute values and the temporal sequence of second quality attribute values.

The methods can include obtaining a set of one or more calibration spectra representative of the solution, and analyzing the set of calibration spectra to determine the first and second sets of principal vibrational components. The first chemometrics model can include a first set of coefficients associated with the first set of principal vibrational components and the second chemometrics model can include a second set of coefficients associated with the second set of principal vibrational components, and the methods can include determining the first and second sets of coefficients based on a regression analysis.

The methods can include analyzing the vibrational spectrum using a third chemometrics model to determine a value of a third quality attribute associated with the solution. The third chemometrics model can include a third set of principal vibrational components correlated with the third quality attribute. The third chemometrics model can include at least three principal vibrational components (e.g., at least five principal vibrational components). Analyzing the vibrational spectrum using the third chemometrics model can include calculating the third quality attribute value based on the third set of principal vibrational components. Calculating the third quality attribute value can include determining the value as a linear function of the third set of principal vibrational components. The methods can include adjusting the at least one parameter based on at least one of the first, second, and third quality attribute values.

The methods can include analyzing the vibrational spectrum using a fourth chemometrics model to determine a value of a fourth quality attribute associated with the solution. The fourth chemometrics model can include a fourth set of principal vibrational components correlated with the fourth quality attribute. The fourth chemometrics model can include at least three principal vibrational components (e.g., at least five principal vibrational components). Analyzing the vibrational spectrum using the fourth chemometrics model can include calculating the value of the fourth quality attribute based on the fourth set of principal vibrational components. Calculating the value of the fourth quality attribute can include determining the value as a linear function of the fourth set of principal vibrational components. The methods can include adjusting the at least one parameter based on at least one of the first, second, third, and fourth quality attribute values.

At least one of the first and second quality attributes can be selected from the group consisting of concentration, aggregates, charge variant distribution, purity, glycan profile, identity, and integrity. At least one of the first and second quality attributes can be selected from the group consisting of protein fragments, nucleic acid fragments, nucleic acid variants, empty capsids, and vector impurities. At least one of the first and second quality attributes can be selected from the group consisting of host cell proteins, residual host DNA, residual column ligands, impurity concentration, impurity amount, residual helper virus, residual helper viral proteins, and residual helper viral DNA.

Embodiments of the methods can also include any of the other features disclosed herein, including combinations of features that are individually disclosed in connection with different embodiments, except as expressly stated otherwise.

In another aspect, the disclosure features biological manufacturing systems that include a bioreactor configured to produce a solution that includes a biological product, a purification unit configured to receive the solution, a radiation source configured to direct radiation to be incident on the solution, a detection apparatus configured to measured radiation from the solution, and a system controller connected to the bioreactor and the detection apparatus, and configured to: receive a measurement signal from the detection apparatus corresponding to information about a vibrational spectrum of the solution; analyze the information using a first chemometrics model to determine value of a first quality attribute associated with the solution; analyze the information using a second chemometrics model to determine a value of a second quality attributed associated with the solution; and adjust at least one parameter of the purification unit based on at least one of the values of the first and second quality attributes.

Embodiments of the systems can include any one or more of the following features.

The systems can include a flow cell positioned so that the solution passes through the flow cell, and the radiation source directs the radiation to be incident on the solution while the solution is in the flow cell.

The biological product can include at least one of a protein-based therapeutic substance, a nucleic acid-based drug substance, and a gene therapy drug substance. The protein-based therapeutic substance can include at least one of a protein, a peptide, an antibody, and an enzyme. The nucleic acid-based drug substance can include at least one of DNA, a plasmid, an oligonucleotide, an aptamer, a DNAzyme, an RNA aptamer, an RNA decoy, a microRNA fragment, and a small interfering RNA fragment.

The first and second quality attributes can each be independently selected from the group consisting of product quality attributes, product-related impurities, and process-related impurities, for a biological product produced by the biological manufacturing system.

The detector can include a total internal reflection sensor configured to measure attenuated totally reflected radiation from the solution. The total internal reflection sensor can be integrated with a portion of the flow cell. The controller and detection apparatus can be configured to measure the attenuated totally reflected radiation from the solution while the solution is flowing within the flow cell. The incident radiation can include infrared radiation.

The first chemometrics model can include a first set of principal vibrational components correlated with the first quality attribute. The first chemometrics model can include at least three principal vibrational components (e.g., at least five principal vibrational components).

The controller can be configured to analyze the vibrational spectrum using the first chemometrics model by calculating the first quality attribute value based on the first set of principal vibrational components. The controller can be configured to calculate the first quality attribute value as a linear function of the first set of principal vibrational components.

The second chemometrics model can include a second set of principal vibrational components correlated with the first quality attribute. The second chemometrics model can include at least three principal vibrational components (e.g., at least five principal vibrational components). The first and second sets of principal vibrational components can have no members in common. The controller can be configured to analyze the vibrational spectrum using the second chemometrics model by calculating the second quality attribute value based on the second set of principal vibrational components. The controller can be configured to calculate the second quality attribute value as a linear function of the second set of principal vibrational components.

The solution can include a solution discharged from the purification unit. The controller can be connected to the purification unit and configured to purify the solution in the purification unit prior to obtaining the information about the vibrational spectrum of the solution.

The purification unit can include a chromatography column. The purification unit can be a first purification unit of the system, and the system can include a second purification unit configured to receive the solution, where the detection apparatus is positioned to measure radiation from the solution as the solution flows between the first purification unit and the second purification unit. The first and second purification units can each include a chromatography column.

The purification unit can be a final purification unit of the system.

The solution can be a first solution, and the detection apparatus can be configured to measure radiation from a second solution, and the controller can be configured to: receive a measurement signal from the detection apparatus corresponding to information about a vibrational spectrum of the second solution; analyze the information about the second solution using the first chemometrics model to determine a value of the first quality attribute for the second solution; and analyze the information about the second solution using the second chemometrics model to determine a value of the second quality attribute for the second solution.

The purification unit can be a first purification unit and the system can include a second purification unit and a third purification unit, where the first solution can flow between the first purification unit and the second purification unit, and the second solution can flow between the second purification unit and the third purification unit. The controller can be configured to adjust the at least one parameter based on at least one of the first and second quality attribute values for the first solution, and the first and second quality attribute values for the second solution.

The detection apparatus and controller can be configured to measure the radiation from the solution and determine the first and second quality attribute values within a time period of 30 seconds or less, starting from a time at which the radiation is incident on the solution. The time period can be 10 seconds or less (e.g., 2 seconds or less).

The detection apparatus and controller can be configured to repeat the steps of measuring the radiation from the solution, analyzing the information about the vibrational spectrum of the solution using the first chemometrics model, and analyzing the vibrational spectrum using the second chemometrics model, to determine a temporal sequence of first quality attribute values and second quality attribute values associated with successive portions of the solution. The control can be configured to adjust the at least one parameter based on at least one of the temporal sequence of first quality attribute values and the temporal sequence of second quality attribute values.

The controller can be configured to obtain a set of one or more calibration spectra representative of the solution, and to analyze the set of calibration spectra to determine the first and second sets of principal vibrational components. The first chemometrics model can include a first set of coefficients associated with the first set of principal vibrational components and the second chemometrics model can include a second set of coefficients associated with the second set of principal vibrational components, and the controller can be configured to determine the first and second sets of coefficients by performing a regression analysis.

The controller can be configured to analyze the information about the vibrational spectrum of the solution using a third chemometrics model to determine a value of a third quality attribute associated with the solution. The third chemometrics model can include a third set of principal vibrational components correlated with the third quality attribute. The third chemometrics model can include at least three principal vibrational components (e.g., at least five principal vibrational components). The controller can be configured to analyze the information about the vibrational spectrum using the third chemometrics model by calculating the third quality attribute value based on the third set of principal vibrational components. The controller can be configured to calculate the third quality attribute value by determining the value as a linear function of the third set of principal vibrational components. The controller can be configured to adjust the at least one parameter based on at least one of the first, second, and third quality attribute values.

The controller can be configured to analyze the information about the vibrational spectrum using a fourth chemometrics model to determine a value of a fourth quality attribute associated with the solution. The fourth chemometrics model can include a fourth set of principal vibrational components correlated with the fourth quality attribute. The fourth chemometrics model can include at least three principal vibrational components (e.g., at least five principal vibrational components). The controller can be configured to analyze the information about the vibrational spectrum using the fourth chemometrics model by calculating the value of the fourth quality attribute based on the fourth set of principal vibrational components. The controller can be configured to calculate the value of the fourth quality attribute by determining the value as a linear function of the fourth set of principal vibrational components. The controller can be configured to adjust the at least one parameter based on at least one of the first, second, third, and fourth quality attribute values.

At least one of the first and second quality attributes can be selected from the group consisting of concentration, aggregates, charge variant distribution, purity, glycan profile, identity, and integrity. At least one of the first and second quality attributes can be selected from the group consisting of protein fragments, nucleic acid fragments, nucleic acid variants, empty capsids, and vector impurities. At least one of the first and second quality attributes can be selected from the group consisting of host cell proteins, residual host DNA, residual column ligands, impurity concentration, impurity amount, residual helper virus, residual helper viral proteins, and residual helper viral DNA.

Embodiments of the systems can also include any of the other features disclosed herein, including combinations of features that are individually disclosed in connection with different embodiments, unless expressly stated otherwise.

As used herein, "real-time" refers to measurements or processes that occur with a relatively small delay or recurrence period. For example, "real-time" measurements are measurements for which a total elapsed time interval between the beginning of the measurement of spectroscopic information and the time at which a parameter value or other quantity is calculated from the information is 1 minute or less. Periodic real-time measurements are recurring/periodic measurements with a time interval of 1 minute or less between successive measurements.

As used herein, "near real-time" measurements are measurements for which a total elapsed time interval between the beginning of the measurement of spectroscopic information and the time at which a parameter value or other quantity is calculated from the information is between 1 minute and 5 minutes. Periodic near real-time measurements are recurring/periodic measurements with a time interval of between 1 minute and 5 minutes between successive measurements.

As used herein, the term "quality attribute" refers to a value of a parameter that is used to assess the operating condition of a bio-manufacturing system, the integrity of a process implemented in such a system, and/or a product derived from such a process. Quality attributes can be product quality attributes which relate to the purity, integrity, yield, and other characteristics of a product produced by a bio-manufacturing system; they can be product-related impurity parameters which provide information about the product that is produced in the system; and they can be process-related purity parameters which provide information about the fidelity of bio-manufacturing processes implemented in the system.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIG. 17 is a table showing antibody concentration values predicted for six samples using a partial least squares model for antibody concentration.

FIGS. 19A-19D are graphs showing measurements of glucose concentration, glutamine concentration, lactate concentration, and ammonium ion concentration for different cell density, pH, and perfusion conditions for a bioreactor producing a monoclonal antibody product.

Like symbols in the drawings indicate like elements.

DETAILED DESCRIPTION

Introduction

Figure 1:
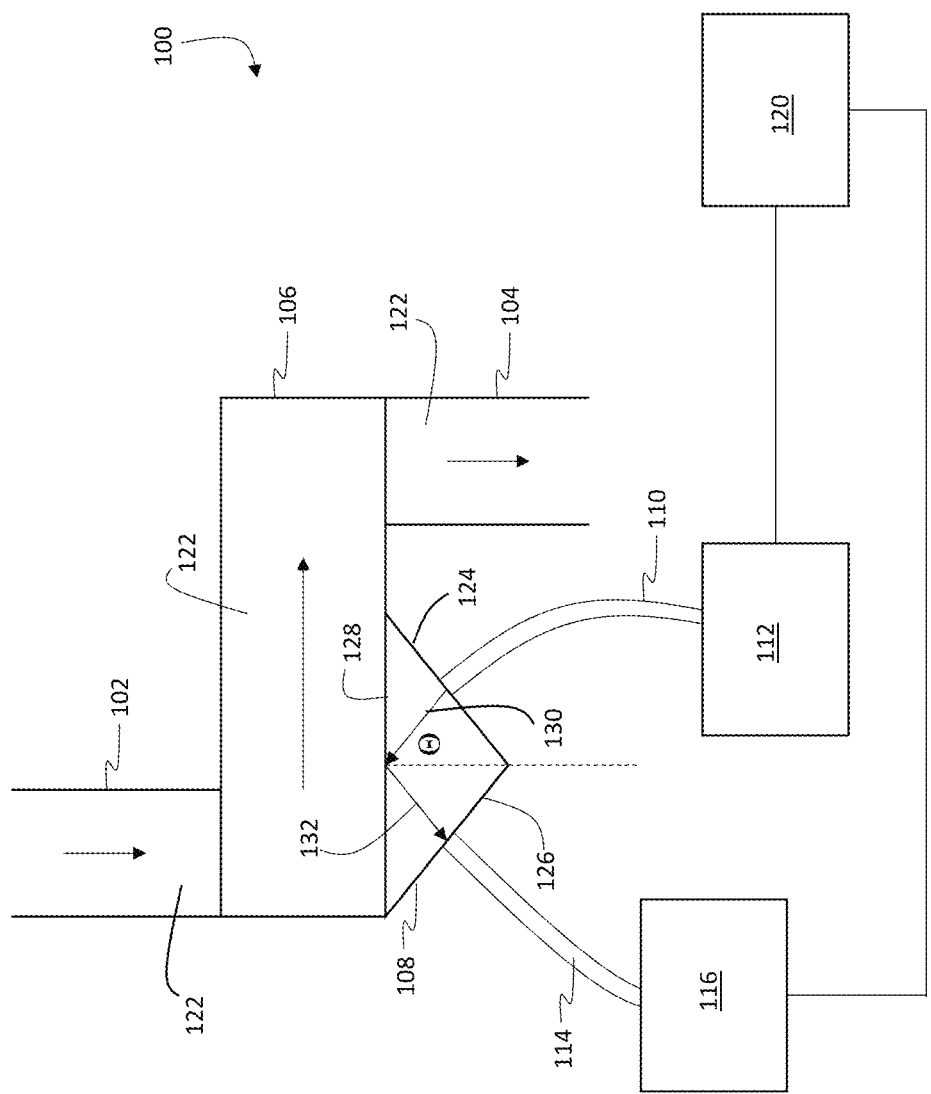
FIG. 1 is a schematic diagram showing an example of a system for measuring infrared spectral information for a process solution in a bio-manufacturing system.

Industrial scale bio-manufacturing can be performed in two-column and multi-column chromatography systems in a variety of configurations. In these complex systems, product yield, quality, and waste rates are functions of a large number of process-related parameters and steps. During manufacturing of therapeutic proteins and other commercially valuable bio-molecules, product outcomes can be strongly influenced by these parameters and steps. Appropriate control over such parameters and steps is therefore an important aspect of large scale manufacturing. Features and aspects of bio-manufacturing systems are disclosed, for example, in PCT Patent Application Publication No. WO 2014/137903, the entire contents of which are incorporated herein by reference.

Exercising appropriate control over bio-manufacturing parameters, including automated control, is facilitated by in-process, in-line monitoring of intermediate solution streams, and specifically, concentrations of intermediates and products in such streams, and other properties (such as pH, for example) of such streams. Conventional methods for solution monitoring include techniques such as UV absorbance measurements. Unfortunately, however, such methods are subject to drift over measurement periods of a few days due to factors such as temperature, humidity, ambient light intensities, and local sample inhomogeneity.

Furthermore, such methods typically do not allow multiple quantities to be calculated or otherwise determined in real-time or near real-time from a single measurement (e.g., a measurement of an absorbance spectrum). Instead, there is generally a 1:1 correspondence between measurements performed and quantities determined from such measurements. Thus, for example, to measure concentrations of two different species in a solution stream, two different UV absorbance measurements would be recorded, and each would yield a concentration value for one of the species. Due to the measurement and analysis time required to determine such values, it may not be possible to determine values of multiple quantities in real-time or near real-time.

Disclosed herein are methods and systems that use infrared spectroscopic measurements in combination with multivariate chemometric models to determine quantitative information about analytes and properties in process solutions. The analytes can include product and intermediate components, waste products, residual reagents, and buffer components, for example. Examples of properties can include, but are not limited to, pH levels, salinity levels, protein/peptide aggregation levels, quantities/concentrations of biological products such as proteins, peptides, and nucleic acids, concentrations/quantities of process and product impurities, and charge variant distributions of proteins.

Infrared spectroscopic measurements can be performed rapidly and with high reproducibility, and calibrated chemometric models are used to predict quality attributes in real-time or near real-time under a variety of biomanufacturing process conditions, and for a variety of reagents, products, by-products, and impurities. The extensive control afforded by the chemometric-based analysis methods disclosed herein allows biomanufacturing processes to be performed more efficiently, with less waste, higher product yields, and greater product purity.

Due to the wavelengths of infrared radiation, infrared spectroscopic measurements generally provide information about vibrational properties of analytes such as reaction products and by-products in process fluids within biomanufacturing systems. While other measurement modalities such as Raman spectroscopy can also yield important information about such analytes, infrared measurements can provide certain advantages in some circumstances. Typically, for example, measurements of infrared spectroscopic information can be performed more quickly (e.g., in approximately 30 s or less) than corresponding Raman measurements, which can take between 10 and 15 minutes. Accordingly, infrared measurements can be better suited for real-time and near real-time process monitoring and control applications.

The application of infrared measurements to upstream and downstream process monitoring in biomanufacturing operations for biological drugs has been very limited to-date due to the implementation of manufacturing processes in aqueous solution, and the strong absorption of water at approximately 1640 $cm^{-1}$. Process water essentially interferes with conventional analytical calculations based on infrared measurements, sometimes to the extent that determination of quantitative information from such measurements is not possible. However, the chemometric methods disclosed herein can reliably predict quantitative values of a variety of parameters even in the presence of strong water absorption. As such, the methods disclosed herein can use infrared spectral measurements for routine, high-throughput process monitoring and control.

In addition, infrared spectroscopic measurements can be more sensitive to changes in analytes and properties of process fluids than Raman measurements. Combined with the rate at which such measurements can be performed, infrared spectroscopic measurements may be better suitable to higher throughput applications during active monitoring of biomanufacturing processes.

Further, infrared spectroscopic measurements are generally less sensitive to variations in environmental conditions that occur as the measurements are performed. Relative to Raman measurements, for example, infrared spectroscopic measurements are typically less sensitive to variations in temperature, humidity, and ambient light. Accordingly, chemometric models based on such measurements—once calibrated—can be used in a greater variety of conditions, and may be easier to transfer from a laboratory to a commercial, high-throughput manufacturing operation.

Infrared Spectroscopic Measurements and Measurement Systems

FIG. 1 is a schematic diagram showing an embodiment of a measurement system 100 for measuring infrared spectral information for a process solution in a biomanufacturing system. System 100 includes a flow cell 106 positioned between fluid conduits 102 and 104. A fluid 122 enters flow cell 106 from conduit 102, flows through cell 106 in the direction shown by the arrows in FIG. 1, and exits cell 106 into conduit 104.

In some embodiments, as shown in FIG. 1, flow cell 106 includes an attenuated total reflection (ATR) interface for measuring infrared spectral information in an ATR configuration/mode. In FIG. 1, the ATR interface is implemented as a prism 108 that forms a portion of an interior cavity within cell 106. A first fiber 110 is optically coupled to a first surface 124 of prism 108 and to a light source 112. A second fiber 114 is optically coupled to a second surface 126 of prism 108 and to a detector 116. Radiation source 112 and detector 116 are electrically connected to a controller 120.

During operation, controller 120 activates radiation source 112 to generate incident radiation 130. Incident radiation 130 is coupled into first fiber 110 and delivered by first fiber 110 into prism 108 through first surface 124. After entering prism 108, incident radiation 130 propagates toward surface 128 of flow cell 106.

The angle of incidence $\theta$ of incident radiation 130 with respect to the normal to surface 128, and the material from which flow cell 106 is formed, are selected such that when incident radiation 130 reaches surface 128, the incident radiation undergoes total internal reflection at surface 128, generating reflected radiation 132. Reflected radiation 132 is coupled into second fiber 114 through surface 126, propagates through second fiber 114, and is detected by detector 116. Detector 116 converts reflected radiation 132 into spectral information and transmits the spectral information to controller 120. As will be explained in greater detail below, controller 120 analyzes the spectral information to determine information about one or more components of fluid 122 and/or one or more process conditions associated with a biomanufacturing process that produces fluid 122.

Radiation source 112 can include a variety of different sources of radiation. In some embodiments, for example, radiation source 112 includes one or more light emitting diodes (LEDs). In general, radiation source 112 generates incident radiation 130 in the infrared region of the electromagnetic spectrum. For example, incident radiation 130 typically includes radiation at one or more wavelengths between 750 nm and 500 microns.

In certain embodiments, radiation source 112 generates incident radiation 130 at multiple, distinct wavelengths. For example, radiation source 112 can generate incident radiation 130 at 3 or more (e.g., 5 or more, 7 or more, 10 or more, 15 or more, 20 or more, or even more) distinct, spectrally separated "bands" or "lines", each of which has a central wavelength within the infrared region of the spectrum.

In some embodiments, radiation source 112 generates broadband incident radiation 130 over a range of wavelengths in the infrared spectral region. For example, incident radiation 130 can have a full-width at half-maximum bandwidth of 100 nm or more (e.g., 200 nm or more, 500 nm or more, 1 micron or more, 5 microns or more, 10 microns or more, 50 microns or more, 100 microns or more, 200 microns or more, 300 microns or more).

Detector 116 can generally be implemented in a variety of ways. In certain embodiments, for example, detector 116 can be a Fourier transform infrared (FTIR) spectrometer that receives reflected radiation 132 and generates spectral information for the reflected radiation. One suitable FTIR spectrometer for use as detector 116 is the Bruker MATRIX-MF® FTIR (available from Bruker Optics, Billerica, MA), with a mercury cadmium telluride (MCT) infrared sensor, although many other FTIR spectrometers can also be used.

Detector 116 can also be implemented using standard optical elements that spatially disperse the frequency components of reflected radiation 132, thereby mapping radiation frequency onto a spatial coordinate direction, and then analyzing the dispersed frequency components as a function of position to measure radiation intensity. Suitable optical elements for spatially dispersing the frequency components of reflected radiation 132 include gratings, prisms, diffractive optical elements, and adaptive modulators such as liquid crystal-based optical modulators. After the frequency components of reflected radiation 132 have been spatially dispersed, the radiation intensity as a function of frequency can be measured using various detectors suitable for use in detecting infrared radiation, including detectors based on one or more of mercury cadmium telluride, indium antimonide, indium arsenide, and lead selenide, and/or detectors featuring sensors based on quantum wells and/or quantum dots.

Figure 2:
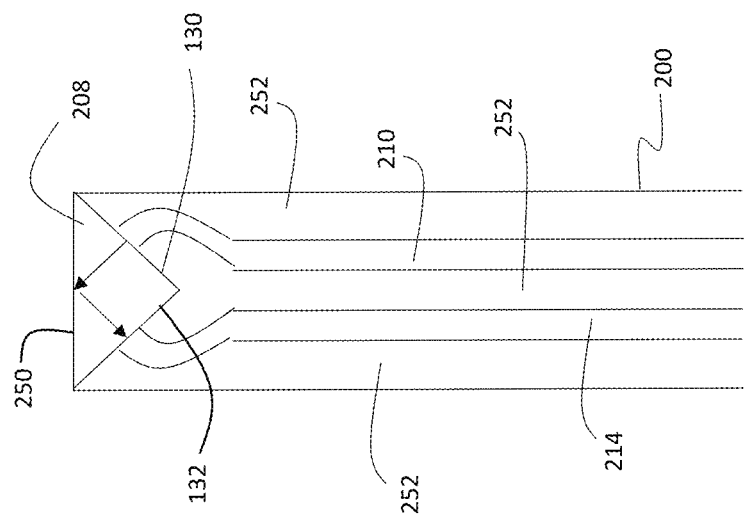
FIG. 2 is a schematic cross-sectional diagram showing an example of a fiber.

As shown in FIG. 1, in some embodiments, incident radiation 130 and reflected radiation 132 can be delivered to and from the ATR interface (e.g., prism 108) through optical fibers 110 and 114. In certain embodiments, however, both incident radiation 130 and reflected radiation can be delivered to and from the ATR interface using a single fiber. FIG. 2 shows a schematic cross-sectional diagram of a fiber 200 that includes a first radiation transporting core 210 and a second radiation transporting core 214, surrounded by an opaque cladding material 252. Integrated into one end of fiber 200 is an ATR interface (implemented as a prism 208). Prism 208 is positioned so that surface 250 can be optically coupled to flow cell 106 of FIG. 1, in place of prism 108.

During operation, incident radiation 130 generated by radiation source 112 is coupled into fiber core 210 and propagates through core 210, reaching integrated prism 208. The incident radiation enters prism 208 and undergoes total internal reflection from surface 250 of prism 208, generating reflected radiation 132. Reflected radiation 132 is coupled into core 214 and propagates back through fiber 200. At the end of fiber 200 opposite to prism 208, reflected radiation 132 is coupled into detector 116 and analyzed as discussed above.

In general, the foregoing examples represent only a subset of the optical fibers and probes that can be used to transport incident radiation 130 and reflected radiation 132 in system 100. A wide variety of fibers and probes can be used, including certain commercially available components. One example of a suitable commercially available probe is the IN350T® diamond ATR probe (available from Bruker Optics).

In addition, in some embodiments, incident radiation 130 and/or reflected radiation 132 can propagate through free space rather than being transported in optical fibers. Free-space propagation can permit additional optical elements such as filters, apertures, beam splitters, mirrors, and lenses to be inserted into the optical path of either or both incident radiation 130 and reflected radiation 132, permitting further control over the properties of both beams.

Figure 3:
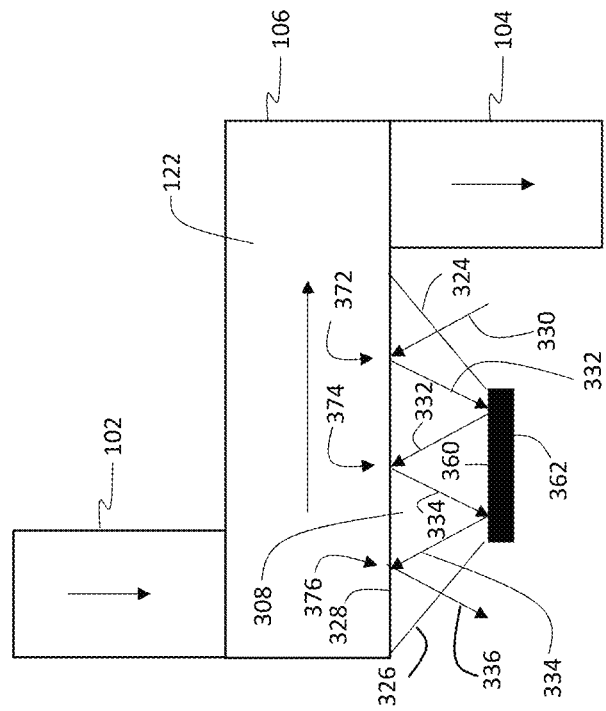
FIG. 3 a schematic diagram showing an example of a prism that forms an attenuated total reflection interface.

As shown in FIGS. 1 and 2, in some embodiments, the ATR interface can be implemented as a prism with geometrical features (e.g., apex angle) selected to ensure that total internal reflection of incident radiation 130 occurs when the incident radiation encounters the interface between the prism material and fluid 122. More generally, the ATR interface can be implemented in other ways as well. FIG. 3 is a schematic diagram showing another example of an ATR interface, implemented as a trapezoid 308 (or alternatively, as a truncated prism). Surface 328 of trapezoid 308 forms a portion of an interior cavity of flow cell 106. In addition, a reflective coating 362 is disposed on surface 360 of trapezoid 308, opposite to surface 328.

During operation, incident radiation 330 is coupled into trapezoid 308 through surface 324 (e.g., from an optical fiber). Incident radiation 330 is incident at a first location 372 along the interface between fluid 122 and surface 328 of trapezoid 308. The incident radiation undergoes total internal reflection at surface 328, forming reflected radiation 332. Reflected radiation 332 is reflected by coating 362 on surface 360, and is incident again at location 374 along the interface between fluid 122 and surface 328 of trapezoid 308. Reflected radiation 334 emerges from location 374, is reflected by coating 362, and is incident at location 376 along the interface between fluid 122 and surface 328. Reflected radiation 336 emerges from location 376 and is coupled out of trapezoid 308 through surface 326 (e.g., into an optical fiber).

The geometrical features of trapezoid 308 ensure that incident radiation 330 interacts multiple times with fluid 122 through surface 328 of trapezoid 308, increasing the signal-to-noise ratio of the spectral information carried by reflected radiation 336, relative to the single-interaction measurements that occur for example in FIG. 1. In general, trapezoid 308 can be configured so that the number of interactions between the incident radiation 330 and fluid 122 through surface 328 is 2 or more (e.g., 3 or more, 5 or more, 7 or more, 10 or more, or even more).

In general, ATR interfaces such as prism 108 and trapezoid 308 for use in system 100 are formed from relatively high refractive index materials to ensure that total internal reflection occurs at the interface between prism 108 and/or trapezoid 308 and fluid 122 (e.g., surface 128 and/or 328). Suitable materials from which ATR interfaces such as prism 108 and/or trapezoid 328 can be formed include, but are not limited to, diamond, germanium, various thallium halides, zinc selenide, and silicon.

In FIG. 1, flow cell 106 is implemented as a flow-through cell connected between conduits 102 and 104. Fluid 122—which can include any one or more of a variety of different process fluids at various locations within a biomanufacturing system—flows through cell 106 as infrared spectral information is measured and analyzed. Flow cell 106 can be positioned at a variety of locations within a biomanufacturing system to allow measurement of spectral information for purposes of product quality assessment and process control. For example, in some embodiments, flow cell 106 can be positioned at an outlet port of a bioreactor (e.g., a perfusion bioreactor such as a tangential flow perfusion bioreactor). Alternatively, or in addition, flow cell 106 can be positioned along a fluid flow path between components of a biomanufacturing system, including between a bioreactor and a purification unit, between two purification units, and/or after a purification units. Biomanufacturing systems can generally include a single flow cell 106 or multiple flow cells 106, each of which is positioned within the biomanufacturing system to measure spectral information at a different location.

Figure 4:
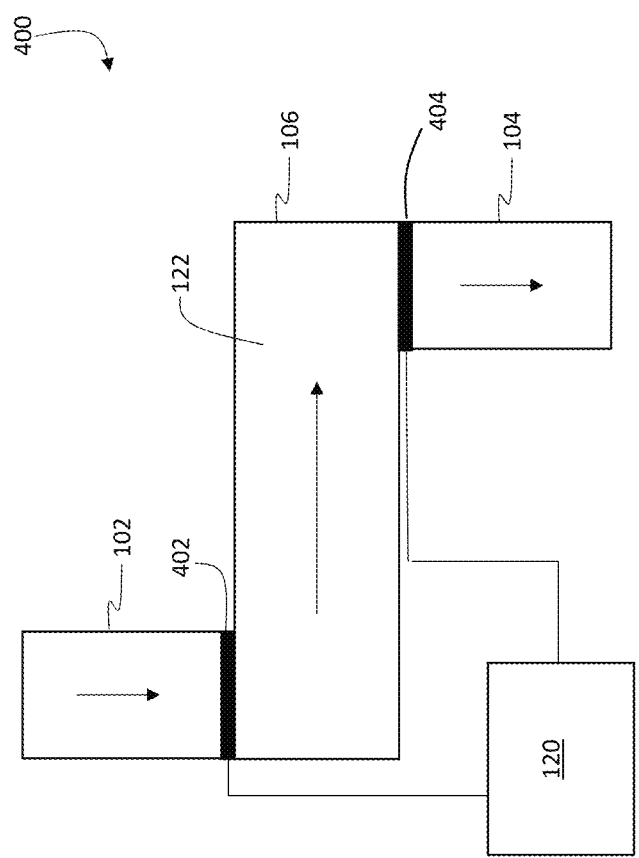
FIG. 4 is a schematic diagram showing an example of a flow cell positioned between two fluid conduits.

In some embodiments, infrared spectral measurements are performed while fluid 122 is not flowing in cell 106. FIG. 4 is a schematic diagram showing a flow cell 106 positioned between two fluid conduits 102 and 104. A first valve 402, electrically connected to controller 120, is positioned between conduit 102 and flow cell 106. A second valve 404, electrically connected to controller 120, is positioned between flow cell 106 and conduit 104. During operation, controller 120 opens valve 402 to admit a portion of fluid 122 into flow cell 106. When the portion of fluid 122 has entered flow cell 106, controller 120 closes valve 402. With valve 404 remaining closed, the portion of fluid 122 is temporarily trapped within flow cell 106. Infrared spectral information for fluid 122 is measured by controller 120 as discussed above with fluid 122 remaining static within flow cell 106, and then controller 120 opens valve 404 to allow the portion of fluid 122 to flow out of cell 106. At the same time or later, controller 120 can also open valve 402 to admit a new portion of fluid 122 into flow cell 106. In this manner, infrared spectral information can be measured from a non-flowing portion of fluid 122, which can be useful when the flow rate of fluid 122 through cell 106 would otherwise perturb or interfere with obtaining accurate, reproducible infrared spectral information from the fluid. Such situations can arise, for example, when fluid flow through cell 106 would be highly turbid, leading to scattering of incident radiation 130 and/or interactions with bubbles and other flow-related inhomogenieties in fluid 122.

Figure 5:
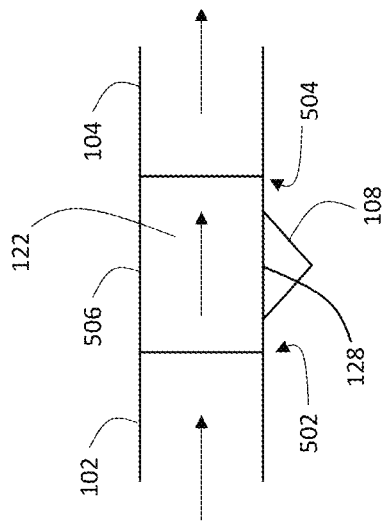
FIG. 5 is a schematic diagram showing another example of a flow cell positioned between two fluid conduits.

While FIG. 1 shows one example of a flow cell 106 that can be used in system 100, more generally flow cells having a variety of different geometries can be used. FIG. 5 is a schematic diagram showing a flow cell 506 positioned between conduits 102 and 104. An ATR interface forms a portion of a cavity or channel wall within flow cell 506. As shown in FIG. 5, fluid 122 flows from conduit 102 through cell 506 and into conduit 104. Infrared spectral measurements are performed via ATR of incident radiation 130 at interface 128 while fluid 122 is flowing, or alternatively, while fluid 122 is static within flow cell 506 (e.g., when valves connected to controller 120 adjust the flow of fluid 122 into and out of flow cell 506, as discussed above.

While flow cell 106 in FIG. 1 defines a non-linear, two-dimensional fluid flow path from conduit 102 through flow cell 106 and into conduit 104, flow cell 506 defines a linear, one-dimension fluid flow path due to the positions of fluid ports 502 and 504 at either end of flow cell 506. For process fluids that flow at relatively higher rates within a biomanufacturing system, flow cell 506 may provide certain advantages relative to flow cell 106. In particular, flow cell 506 may allow a higher aggregate fluid flow rate to be maintained, thereby ensuring that infrared spectral measurements do not introduce a flow-rate bottleneck into a continuous biomanufacturing process.

Figure 6:
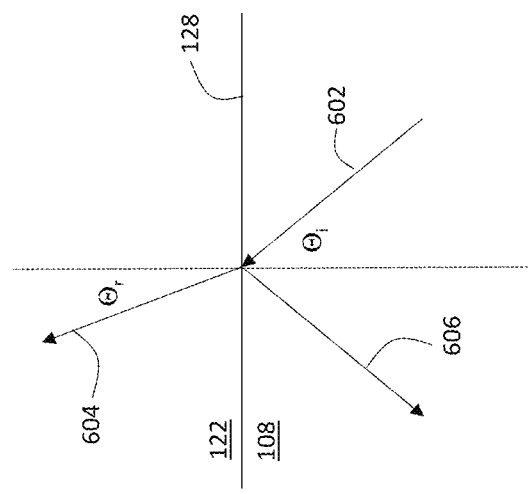
FIG. 6 is a schematic diagram showing a ray of incident radiation that refracts at the surface of a prism.

As discussed above, certain measurement systems disclosed herein are configured to perform infrared spectroscopic measurements using an ATR-based geometry. The ATR geometry takes advantage of a mismatch in refractive indices between the material from which the ATR interface (e.g., prisms 108 and 308) is formed and fluid 122. FIG. 6 is a schematic diagram showing a ray 602 of incident radiation 130 that is incident on surface 128 of prism 108. Surface 128 forms the boundary between the material from which prism 108 is formed (generally, a material having a relatively high index of refraction at the wavelength of ray 602) and fluid 122 (which generally has a comparatively smaller index of refraction). Snell's law describes the relationship between the angles of incidence and reflection at the interface, $\theta_i$ and $\theta_r$, and the indices of refraction $n_p$ and $n_f$ of the prism and fluid, respectively:

$$n_p \sin \theta_i = n_f \sin \theta_r \qquad [1]$$

As the value of $n_p$ increases relative to the value of $n_f$, the value of $\sin \theta_r$ increases to maintain the relationship in Equation (1). In other words, the larger the refractive index mismatch between prism 108 and fluid 122, the larger the value of $\sin \theta_r$, which means that the angle of refraction $\theta_r$ increases. For fixed values of $n_p$ and $n_f$, the angle of incidence $\theta_i$ can be selected such that $\sin \theta_r = 1$. That is, the refracted ray 604 propagates in a direction tangential to surface 128. This angle of incidence is referred to as the critical angle, $\theta_c$.

For angles of incidence larger than the critical angle, no refracted ray 604 is generated at surface 128. Instead, incident ray 602 undergoes total internal refraction at surface 128, producing a reflected ray 606. However, at surface 128, an evanescent field extends for a short distance—often referred to as a penetration depth—beyond the interface and into fluid 122. No energy flows across the interface. Nonetheless, the evanescent field interacts with fluid 122 (and components of the fluid) and the spectral properties of the field are modified by this interaction. As a result, by analyzing variations in the spectral properties of reflected ray 606, information about various components (such as analytes and manufacturing by-products) and fluid attributes can be extracted.

In some embodiments, the measurement of infrared spectroscopic information using ATR geometry can provide certain advantages. For example, relative to transmission-mode infrared spectroscopic measurements, the ATR geometry involves a penetration depth by the evanescent field into the fluid that is interrogated that is relatively short compared to conventional absorptive path lengths used in transmission-mode experiments. In general, the longer the path length, the greater the reduction in sensitivity of the measurement. Thus, in certain embodiments, ATR-based infrared spectroscopic measurements can be performed at higher sensitivity than transmission-mode infrared absorption measurements.

Figure 7:
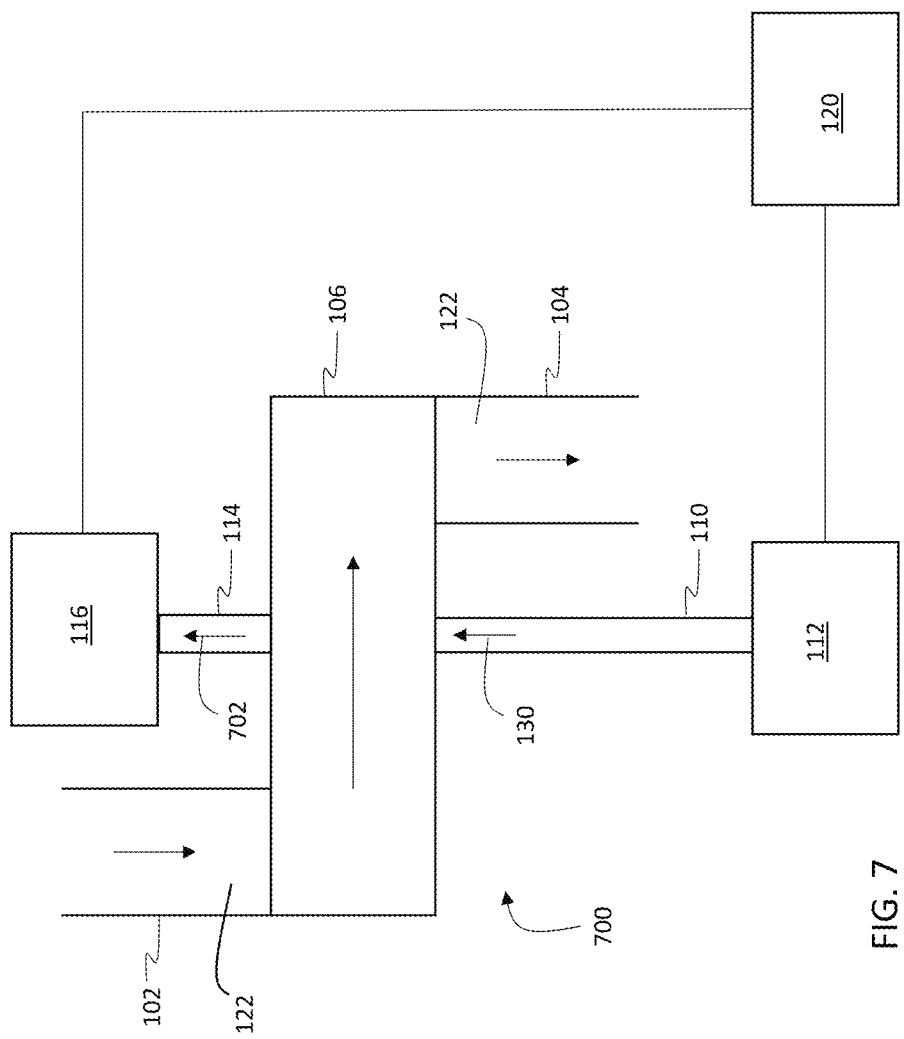
FIG. 7 is a schematic diagram showing an example of a measurement system that measures infrared spectroscopic information for a fluid in a bio-manufacturing system.

Nonetheless, in some embodiments, chemometrics-based analysis can be performed on infrared spectroscopic information acquired via transmission-mode measurements. FIG. 7 shows a schematic diagram of a measurement system 700 for use with a biomanufacturing system. System 700 measures infrared spectroscopic information for fluid 122 via a transmission-mode measurement geometry.

Fluid 122 flows from conduit 102 through flow cell 106 and into conduit 104. Controller 120 activates radiation source 112 which generates incident radiation 130. Incident radiation 130 propagates through fiber 110 and is coupled through a window that forms a portion of a wall of flow cell 106 and into an interior cavity or channel within flow cell 106. Once inside the flow cell, at least a portion of incident radiation 130 is absorbed by one or more analytes or other components of fluid 122. The non-absorbed portion of incident radiation 130 emerges through a second window in flow cell 106 as transmitted radiation 702, and propagates through second fiber 114 to detector 116. Electrical signals encoding the infrared spectroscopic information carried by transmitted radiation 602, generated by detector 116, are transmitted to controller 120 for analysis.

Chemometrics-Based Analysis of Infrared Spectroscopic Information

Predictive, chemometrics model-based analysis of spectroscopic measurements for purposes of process analytics in the manufacturing of small-molecule pharmaceutical substances has enjoyed some success. However, such methods have not been applied to the development of larger biotherapeutics such as antibody-based drugs because such products are large in size, complex, and heterogeneous. Further, biomanufacturing processes for such substances are more complex than for small-molecule pharmaceuticals, and yield process solutions containing a wide range of analytes and other substances. To-date, these complexities have counseled against the application of chemometrics methods to process control for the biomanufacturing of large biological molecules such as antibody-based pharmaceuticals and nucleic acid-based products.

However, it has been discovered that despite the foregoing complications, chemometrics model-based analysis of spectroscopic measurements can yield values of a variety of process-related parameters and product attributes associated with the biomanufacturing of large biological molecules. These parameters and attributes can be used to process feedback and control in real time or near real-time. In particular, vibrational spectroscopic information derived from infrared reflectance (or absorption) measurements is particularly amenable to chemometrics model-based analysis, as the spectroscopic information provides a rich data set with prominent features such as stretching and bending resonances that are directly associated with particular analytes and by-products. More generally, the spectroscopic information encodes a complex set of responses of process fluid components to incident infrared radiation, and multivariate data analysis tools can decode these responses and, for certain parameters, be used predictively with high accuracy.

In this section, methods and systems for constructing and applying chemometrics models to infrared spectroscopic information are discussed. The methods and systems are particularly well-suited for generating values of a variety of product attributes and parameters associated with process fluids generated during continuous biomanufacturing operations, and can be used to monitor such operations and perform process control via adjustment of various biomanufacturing process inputs and properties. In particular, the methods can be used for biomanufacturing process feedback and control in real time or near-real time.

As will be described in greater detail below, the multivariate data analysis methods discussed herein are used to isolate responses in spectral information that are attributable to different analytes and quality attributes. After chemometric models have been constructed for each analyte and/or quality attribute from data obtained from a reference method (such as chromatography or mass spectrometry), then a single set of spectral information (e.g., an infrared absorbance or reflectance spectrum) can be obtained, and the spectral information can be processed using the chemometric models to predict quantitative values of each of the quality attributes corresponding to the models from the same set of spectral information. Because the models operate on the same set of information, predictive determination of the values of the quality attributes can occur in real-time or near real-time.

The chemometrics model-based analytical methods discussed in this section operate on infrared spectroscopic information to determine values of process-related parameters. The infrared spectroscopic information can be measured as described in the previous section, or by using other methods. Typically, the infrared spectroscopic information corresponds to vibrational spectroscopic information, and more particularly, to a vibrational spectrum of a process fluid (and the components contained within the fluid). A vibrational spectrum is a two-dimensional data set that includes intensity values as a function of radiation wavelength or frequency, where the range of wavelengths or frequencies falls within the infrared portion of the electromagnetic spectrum and therefore corresponds to typical wavelengths or frequencies of different vibrational modes of components of the process fluid.

More generally, as used herein, vibrational spectroscopic information includes any data set that represents vibrational responses (e.g., different vibrational modes) of components of a process fluid. The vibrational spectroscopic information can be encoded as a conventional vibrational spectrum, or in a different form which represents similar information content to a vibrational spectrum.

Figure 8:
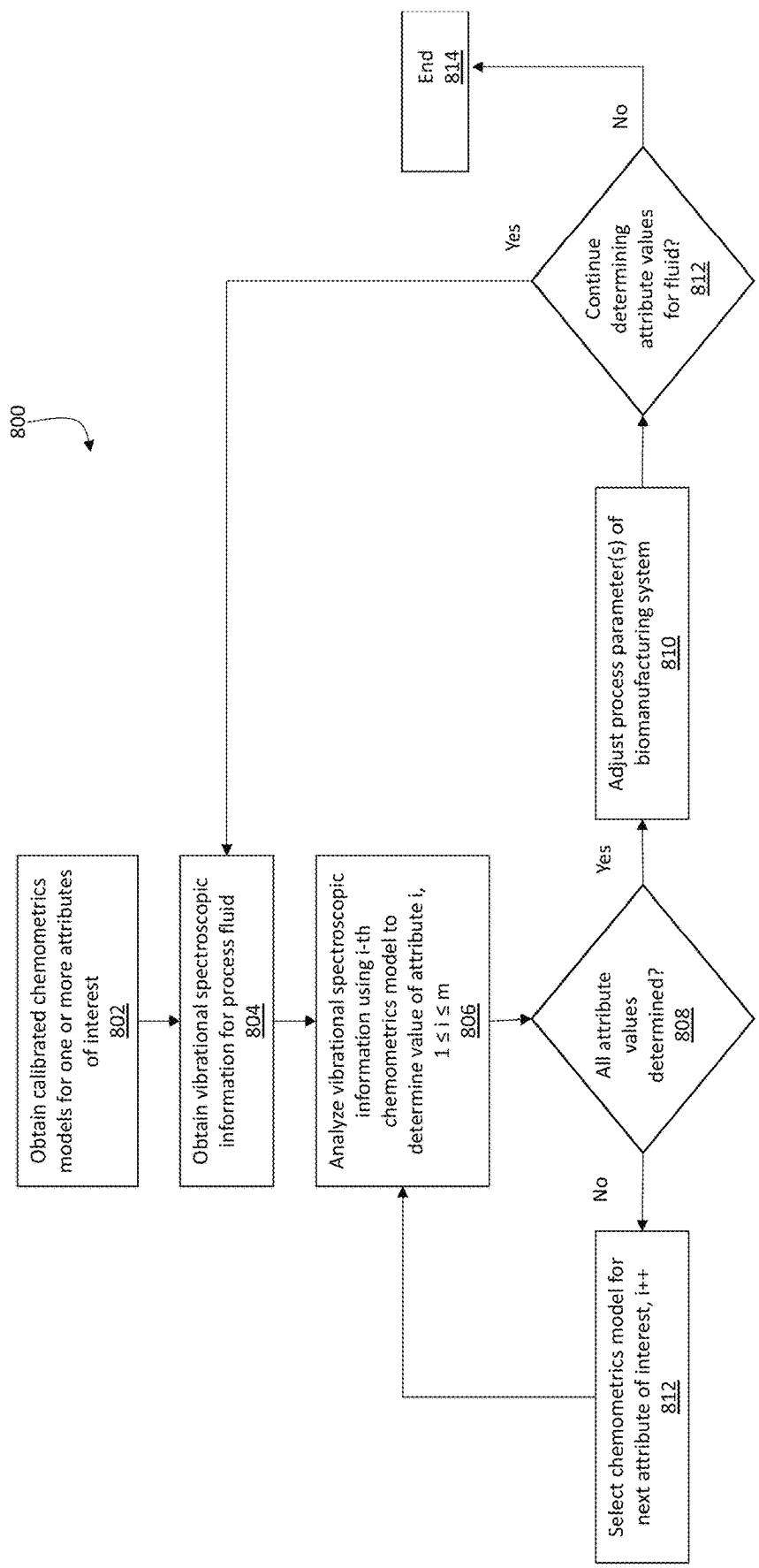
FIG. 8 is a flow chart that shows example steps that can be performed to analyze vibrational spectroscopic information of a process fluid.

FIG. 8 is a flow chart 800 that shows a series of example steps that can be performed to analyze vibrational spectroscopic information (such as a vibrational spectrum) of a process fluid and its associated components to determine values of various attributes of the fluid and its associated components. Each of the steps shown in flow chart 800 can be executed by a system controller, such as controller 120, in automated fashion to perform the analysis.

In a first step 802, calibrated and validated chemometrics models for each of the attribute values to be determined are obtained. In some embodiments, the chemometrics models—which typically consist of calibrated coefficients describing a functional relationship between the value of an attribute of the process fluid and spectroscopic intensity values at one or more wavelengths or frequencies—can be obtained by retrieving previously stored values of the coefficients from a storage medium. Alternatively, in certain embodiments, the chemometrics models are constructed and validated prior to being used predictively by controller 120.

Figure 9:
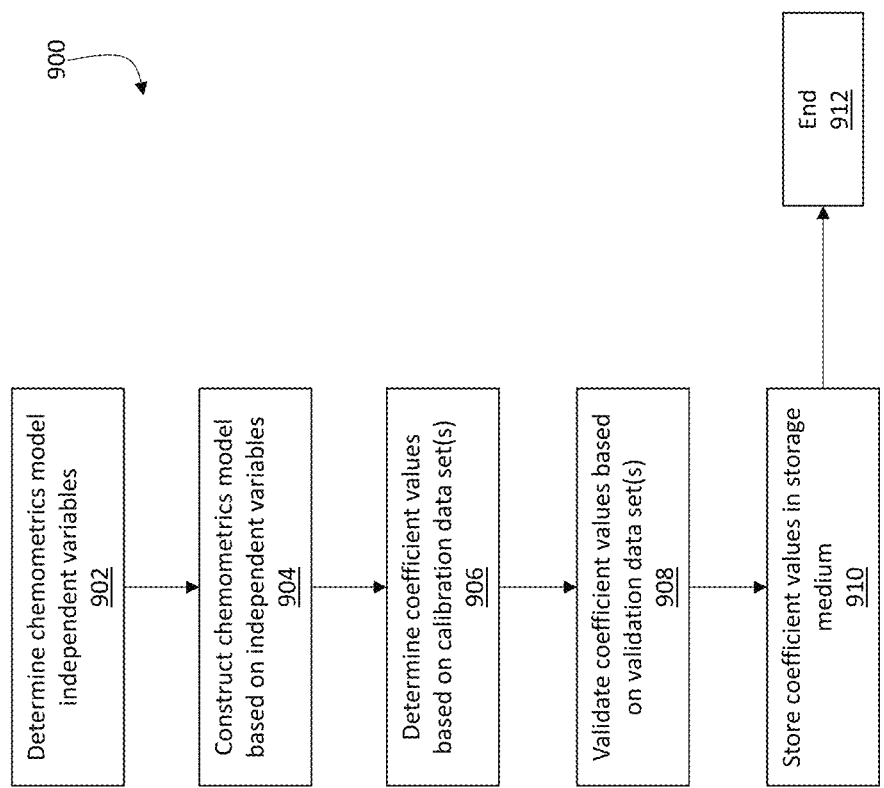
FIG. 9 is a flow chart that shows example steps that can be performed to construct and validate a chemometrics model for an attribute of a process fluid based on vibrational spectroscopic information measured for the process fluid.

FIG. 9 is a flow chart that shows a series of example steps that can be performed to construct and validate a chemometrics model for an attribute of a process fluid based on vibrational spectroscopic information measured for the process fluid. In a first step 902, controller 120 determines a set of characteristic model independent variables. In practice, the set of model variables corresponds to the set of independent vibrational frequencies within the vibrational spectroscopic information that are predictive of the attribute for which the model is constructed. It should be understood that while the following discussion refers to "frequencies" within the vibrational spectroscopic information, the discussion could also equivalently refer to "wavelengths" given the reciprocal relationship between wavelength and frequency in vibrational spectroscopic information. That is, methods in which chemometrics models are defined in terms of a set of frequencies are equivalent to methods in which chemometrics models are defined in terms of a set of wavelengths.

The set of independent vibrational frequencies can be determined in a variety of ways. For example, in some embodiments, the set of vibrational frequencies can be determined by performing a principal components analysis on multiple calibration data sets, each of which corresponds to vibrational spectroscopic information related to a process fluid with a different, known value of the attribute of interest. The principal components analysis determines how many independent frequencies are reliably predictive of the attribute value across each of the calibration data sets, and the values of the independent frequencies. The set of principal components corresponds to the set of frequencies that form the independent model variables in step 902. Methods for performing principal components analysis are discussed, for example, in Bro et al., "Principal component analysis," *Anal. Methods* 6:2812-2831 (2014), and in Chatfield et al., "Principal component analysis," in *Introduction to Multivariate Analysis*, Springer, pp. 51-87 (1980), the entire contents of each of which are incorporated herein by reference.

Next, in step 904, the chemometrics model for the attribute of interest is constructed based on the set of independent variables from step 902. In general, chemometrics models can take a variety of functional forms. One such form is a linear model in which the value of the attribute of interest, A, is expressed as a linear function of the set of independent variables:

$$A = a_1 I_{v1} + a_2 I_{v2} + \ldots + a_i I_{vi} + \ldots + a_n I_{vn} \quad [2]$$

where $v_1 \ldots v_n$ are a set of n frequencies corresponding to the set of independent variables determined in step 902 (i.e., a set of n principal components), and $I_{v1} \ldots I_{vn}$ are a set of n intensity values from the vibrational spectroscopic information corresponding to each of the n frequencies. The parameters $a_1 \ldots a_n$ are a set of coefficients that effectively weight the contribution of each intensity value from the vibrational spectroscopic information to the prediction of the attribute value, A.

In general, as shown by Equation (2), the chemometrics model for the value of attribute A is a multivariate model in which the value of attribute A depends on multiple independent variable values. The number of independent variables in the chemometrics model can generally be selected as desired based on, for example, the results of a principal components analysis. Thus, for example, the value of attribute A in the chemometrics model can be expressed as a function of one or more (e.g., two or more, three or more, four or more, five or more, six or more, seven or more, eight or more, ten or more, 12 or more, 15 or more, 20 or more, or even more) independent variables.

In some embodiments, chemometrics models have a more complex form than the linear form of Equation (2). For example, certain chemometrics models can be non-linear, in which the value of the attribute of interest, A, is expressed as a non-linear function of the set of independent variables. Such functional forms for the chemometric model can be expressed as follows:

$$A = f_1(I_{v1}) + f_2(I_{v2}) + \ldots + f_i(I_{vi}) + \ldots + f_n(I_{vn}) \quad [3]$$

where each of the functional forms, $f_j(I_{vj})$, is linear or non-linear in $I_{vj}$. For Equation (3) to represent a nonlinear chemometric model for A, at least one of the $f_j(I_{vj})$ is a nonlinear function of $I_{vj}$.

In general, each of the $f_j(I_{vj})$ functional forms can be linear or non-linear in N. Where $f_j(I_{vj})$ is a non-linear function of $I_{vj}$, $f_j(I_{vj})$ can have any of a variety of different forms such as, but not limited to, an exponential form, a logarithmic form, a polynomial form, a power law form, a trigonometric form, a hyperbolic form, and any combination of any of the foregoing functional forms. Such functional forms can generally be selected as desired during construction of the chemometric models to ensure that the predictive capabilities of the models for values of attribute A are sufficiently accurate. The subsequent discussion focuses on the linear example of Equation (2), but it should be appreciated that similar principles apply to non-linear chemometrics models as well. That is, non-linear chemometrics models—like linear chemometrics models—have coefficients that are determined from calibration data sets, and are then used to predict quality attribute values from measured vibrational (i.e., infrared) spectroscopic information.

Returning to the linear model of Equation (2), in the next step 906, after the model has been constructed, the coefficient values are determined based on one or more calibration data sets. The following discussion assumes that chemometrics model for attribute A is a linear model defined according to Equation (2) above. If the model is different, the methods discussed below can be used with slight modifications to determine the coefficient values.

Each calibration data set corresponds to a set of vibrational spectral information (e.g., a vibrational spectrum) for a process fluid with a different, known value of attribute A. Referring to Equation (2), for each calibration data set, the values of A and $I_{v1} \ldots I_{vn}$ are known. Thus, in step 906, a single set of coefficient values $a_1 \ldots a_n$ are determined in self-consistent fashion across each calibration data set so that Equation (2) determines, as correctly as possible, each known value of attribute A for each calibration data set.

Various methods can be used to determine the set of coefficient values $a_1 \ldots a_n$ across all calibration data sets. In some embodiments, for example, partial least-squares regression analysis is used simultaneously across all calibration data sets, minimizing the sum of squared error terms for each value of attribute A. Methods for performing partial least-squares regression are described, for example, in Haenlein et al., "A Beginner's Guide to Partial Least Squares Analysis," *Understanding Statistics* 3(4):283-297 (2004), and in Sellin, "Partial Least Squares Analysis," *Int. J. Educational Research* 10(2): 189-200 (1986), the entire contents of each of which are incorporated herein by reference.

Next, in step 908, the set of coefficient values $a_1 \ldots a_n$ determined in step 906 can optionally be validated against one or more additional calibration data sets to verify that the chemometrics model for attribute A predicts attribute values to within an acceptable error. This validation step involves using the chemometrics model to predict one or more values of attribute A for a process fluid based on one or more sets of calibration data (each of which is a set of vibrational spectroscopic information) for the process fluid. Since the value of attribute A is known for each process fluid for which a calibration data set is measured, the accuracy of predicted values of attribute A generated by the chemometrics model can readily be assessed.

In optional step 910, the set of coefficient values $a_1 \ldots a_n$ can be stored in a storage medium for later retrieval by controller 120. The process shown in flow chart 900 ends at step 912.

In some embodiments, both the calibration data set(s) and the measured vibrational spectroscopic information can be processed prior to use in constructing chemometrics models and/or generating predictive quality attribute values from the measured information. In general, a variety of processing steps can be implemented. In some embodiments, for example, calibration data set(s) and/or measured spectroscopic information can be baseline-corrected. In certain embodiments, processing steps such as mean normalization and/or derivatization can be performed on the data sets(s) and/or measured information. Such steps can be performed, for example, using commercial analytical software such as MATLAB® (available from MathWorks, Natick, MA).

In certain embodiments, a chemometrics model that is predictive for values of an attribute A may also be specific to certain conditions under which spectroscopic information is measured. For example, the model may be tied to a particular process fluid in which the information is measured (e.g., a fluid eluting from a particular chromatography column). Accordingly, in some embodiments, the methods disclosed herein include the generation of more than one chemometrics model for predicting values of attribute A.

As an example, a first chemometrics model may be generated to predict a concentration of A in a process fluid eluting from a first chromatography column in a biomanufacturing system, and a second chemometrics model may be generated to predict a concentration of A in a different process fluid eluting from a second chromatography column downstream from the first column. Due to the different compositions of the fluids eluting from the two columns, the chemometrics models can be different, but each is specifically generated to accurately predict values of attribute A at a certain measurement location in the system. Where multiple models for attribute A are generated, each of the models can optionally be stored.

Returning to FIG. 8, after calibrated chemometrics models have been obtained for each attribute of interest, vibrational spectroscopic information for a process fluid is obtained in step 804. As an example, infrared reflectance measurements using the ATR geometry—as discussed above—can be used to obtain the vibrational spectroscopic information, which can correspond to a vibrational spectrum of the process fluid and its associated components.

Next, in step 806, the vibrational spectroscopic information is analyzed using a first chemometrics model obtained in step 802 to determine a value of a first attribute of interest for the fluid. As discussed above in connection with flow chart 900, determining the value of each attribute A involves calculating the value of A using the measured set of intensity values $I_{v1} \ldots I_{vn}$ at each of the independent frequency variables from the vibrational spectroscopic information, and the set of coefficients $a_1 \ldots a_n$ determined for the chemometrics model. Because the calculation is deterministic (e.g., whether the chemometrics model is linear as in Equation (2) or more complex), it is performed very rapidly by controller 120.

After the value of the first attribute is determined, control passes to decision step 808. If additional attribute values for the process fluid are to be determined, then the chemometrics model for the next attribute of interest is selected in step 812, and control returns to step 806, where the value of the next attribute value of interest is determined. Where a total of m attribute values are determined for a process fluid, m different chemometrics models are applied to the vibrational spectroscopic information in step 806.

A significant advantage of the methods and systems disclosed herein is that, due to the richness of the vibrational spectroscopic information, each of the m attribute values can be obtained from the same set of vibrational spectroscopic information. That is, new measurements are not performed to determine each attribute value. Instead, the vibrational spectroscopic information is measured only once, and multiple attribute values—each of which can be determined based on a set of multiple independent variables—are determined from the same set of vibrational spectroscopic information. Because the information measurement is generally the most time-consuming step in the process of determining attribute values, the elapsed time period over which multiple attribute values are determined can be considerably shorter than comparable time periods associated with methods in which multiple measurement steps are involved.

In some embodiments, for example, the elapsed time period during which the vibrational spectroscopic information is obtained and one or more attribute values are determined from the vibrational spectroscopic information using chemometric models is 30 seconds or less (e.g., 25 seconds or less, 20 seconds or less, 15 seconds or less, 10 seconds or less, 5 seconds or less, 2 seconds or less), starting from a time at which incident radiation 130 is incident on the surface of the ATR interface that contacts fluid 122.

If all attribute values of interest have been determined in step 808, control passes to step 810. In step 810, controller 120 adjusts one or more process parameters of the biomanufacturing system in response to the measured attribute values of the process fluid. In general, a wide variety of adjustments can be performed based on the nature of the attribute values that are determined, and the implications of those attribute values with respect to the biomanufacturing process. Certain examples of measured attributes and corresponding adjustments to the biomanufacturing system are discussed in a subsequent section.

Next, in decision step 812, if determination of attribute values for the process fluid is to continue (e.g., for continuous process monitoring and control), control returns to step 804 and new vibrational spectroscopic information for the process fluid is obtained after an appropriate time interval. Alternatively, if determination of attribute values is not to continue, control passes to step 814, where the process of flow chart 800 ends.

In general, the process shown in flow chart 800 can be used to determine any number of attribute values from the same set of vibrational spectroscopic information. For example, in some embodiments, 1 or more attribute values (e.g., 2 or more attribute values, 3 or more attribute values, 4 or more attribute values, 5 or more attribute values, 6 or more attribute values, 8 or more attribute values, 10 or more attribute values, 12 or more attribute values, or even more attribute values) can be determined from the same vibrational spectroscopic information using different chemometric models.

Typically, the set of independent variables that is associated with a given chemometrics model is different from the sets of independent variables associated with other chemometrics models used to calculate different attribute values from the same set of vibrational spectroscopic information. For each chemometrics model, the set of independent variables associated with the model can include two or more (e.g., three or more, four or more, five or more, six or more, eight or more, 10 or more, 12 or more, 15 or more, or even more) principal vibrational components.

However, because the sets of independent variables are generally determined independently for each chemometrics model, the sets of principal vibrational components associated with different chemometrics models may have no members in common. Alternatively, in some embodiments, set of principal vibrational components associated with different chemometrics models may have 1 or more (e.g., 2 or more, 3 or more, 4 or more, 5 or more) members in common.

Chemometric Models for Process Fluid and Component Attributes

In general, chemometrics models can be constructed to determine a wide variety of different quality attributes associated with biomanufacturing processes. These quality attributes typically fall into one several categories including, but not limited to: product quality attributes, which are related to the purity, integrity, yield, morphology, and other attributes of products of the biomanufacturing processes; product-related impurities, which are related to the nature of different synthesis by-products present in process fluids that are produced from biomanufacturing processes; and process-related impurities, which are related to by-products and other undesirable species that result from process conditions within the system.

Chemometrics models can generally be constructed for application to biomanufacturing of a large number of different species. Some of the quality attributes associated with different categories of species are different, and some are similar. For example, in some embodiments, the methods disclosed herein can be applied to the biomanufacturing of protein therapeutic substances such as antibodies, peptides, enzymes, and other species with amino acid chains. For such substances, chemometric models can be constructed to predict values of quality attributes that include: (a) product quality attributes including concentration, aggregates, charge variant distribution, purity, glycan profile, identity, and integrity; (b) product-related impurities such as protein fragments; and (c) process-related impurities such as host cell proteins, residual host cell DNA, residual column ligands (e.g., Protein A), and other impurities such as buffer components, surfactants, process additives such as insulin, poloxamers, detergents, Polysorbate 80, and other compounds from bioreactors and chromatography/separation columns.

In certain embodiments, the methods disclosed herein can be applied to the biomanufacturing of nucleic acid drug substances, including DNA-based species such as DNA, plasmids, oligonucleotides, aptamers, and DNAzymes (e.g., DNase), and RNA-based species such as RNA aptamers, RNA decoys, microRNAs, and small interfering RNAs. For such substances, chemometric models can be constructed to predict values of quality attributes that include: (a) product quality attributes including concentration, identity, integrity, and aggregates; (b) product-related impurities such as nucleic acid fragments and nucleic acid variants; and (c) process-related impurities such as residual column ligands, and other impurities such as buffer components, surfactants, process additives such as insulin, poloxamers, detergents, Polysorbate 80), and other compounds from bioreactors and chromatography/separation columns.

In some embodiments, the methods disclosed herein can be applied to the biomanufacturing of gene therapy drug substances. For such substances, chemometric models can be constructed to predict values of quality attributes that include: (a) product quality attributes such as concentration, aggregates, identity, and integrity; (b) product-related impurities such as empty capsids, fragments, and vector impurities; and (c) process-related impurities such as host cell proteins, host cell DNA, residual helper virus, residual helper viral proteins, residual helper viral DNA, and other impurities such as buffer components, surfactants, process additives such as insulin, poloxamers, detergents, Polysorbate 80), and other compounds from bioreactors and chromatography/separation columns.

Values of any of the foregoing quality attributes can be predictively generated by a suitable chemometrics model. Thus, attribute A in Equations (2) and (3) can represent any of the above quality attributes.

Further, it should be noted that chemometrics models can be constructed to predictively generate values of combinations of any of the above quality attributes from a single set of measured spectroscopic information (e.g., an infrared vibrational spectrum). In general, values of combinations of any two or more (e.g., three or more, four or more, five or more, six or more, seven or more, eight or more, ten or more, or even more) of the above quality attributes can be generated from the same spectroscopic information by suitably constructed chemometrics models.

In the following discussion, specific examples of quality attributes associated with the biomanufacturing of a protein-based therapeutic substance are provided. Spectroscopic measurements are performed on process fluid 122 (and components thereof). The values of the quality attributes determined from the spectroscopic information measured can be used for a variety of purposes, including product quality assessment, biomanufacturing process adjustment, and process termination. Aspects of the use of values of quality attributes for biomanufacturing process adjustment by controller 120 will be discussed later.

(i) Antibody Concentration Value

In certain embodiments, such as when the desired product of a biomanufacturing process is an antibody-based pharmaceutical product, the antibody concentration value of a process fluid at a certain location within a biomanufacturing system can be related to the overall yield of the desired product. Accordingly, in some embodiments, the methods disclosed herein include obtaining and applying a chemometrics model to determine an antibody concentration value for a process fluid.

The set of independent vibrational frequencies that are used in the chemometrics model for the antibody concentration value can include frequencies within specific frequency ranges. By including frequencies within these specific ranges, predictive errors associated with determining antibody concentration values from vibrational spectroscopic information can be reduced.

For example, in some embodiments, the set of principal vibrational frequencies or components used in the chemometrics model for the antibody concentration value can include vibrational spectroscopic information in at least one of a wave number range from 1100 $cm^{-1}$ to 1595 $cm^{-1}$, and a wave number range from 1600 $cm^{-1}$ to 1700 $cm^{-1}$. In certain embodiments, the set of principal vibrational frequencies or components includes at least one component that corresponds to vibrational spectroscopic information in a wave number range from 1100 $cm^{-1}$ to 1595 $cm^{-1}$, and at least one component that corresponds to vibrational spectroscopic information in a wave number range from 1600 $cm^{-1}$ to 1700 $cm^{-1}$.

(ii) Extent of Protein Aggregation

In certain embodiments, such as when the desired product of a biomanufacturing process is protein-based, the extent of protein aggregation in a process fluid can provide important information about protein interaction and product yield. Thus, in some embodiments, the methods disclosed herein include obtaining and applying a chemometrics model to determine an extent of protein aggregation in a process fluid.

The set of independent vibrational frequencies that are used in the chemometrics model for the extent of protein aggregation can include frequencies within specific frequency ranges. For example, in some embodiments, each of the principal vibrational frequencies or components used in the chemometrics model for the extent of protein aggregation corresponds to vibrational spectral information in at least one of a the wave number ranges from 1393 $cm^{-1}$ to 1554 $cm^{-1}$, a range from 1600 $cm^{-1}$ to 1635 $cm^{-1}$, and a range from 844 $cm^{-1}$ to 1180 $cm^{-1}$.

In certain embodiments, at least one of the set of principal vibrational frequencies or components used in the chemometrics model for the extent of protein aggregation corresponds to vibrational spectral information in a frequency range from 1393 $cm^{-1}$ to 1554 $cm^{-1}$, at least one of the principal vibrational frequencies or components corresponds to vibrational spectral information in a frequency range from 1600 $cm^{-1}$ to 1635 $cm^{-1}$, and at least one of the principal vibrational frequencies or components corresponds to vibrational spectral information in a frequency range from 844 $cm^{-1}$ to 1180 $cm^{-1}$.

(iii) Host Cell Protein Quantity

In certain embodiments, the host cell protein quantity for a process fluid in a biomanufacturing system can be used by controller 120 to adjust manufacturing process parameters to improve product yields reduce by-product formation. Thus, the methods disclosed herein can include obtaining and applying a chemometrics model to determine a host cell protein quantity in a process fluid.

The set of independent vibrational frequencies that are used in the chemometrics model for the host cell protein quantity can include frequencies within specific frequency ranges. For example, in certain embodiments, each of the principal vibrational frequencies or components used in the chemometrics model for the host cell protein quantity can correspond to vibrational spectral information in at least one of a wavenumber range from 1500 $cm^{-1}$ to 1600 $cm^{-1}$, a wavenumber range from 1600 $cm^{-1}$ to 1680 $cm^{-1}$, a wavenumber range from 1414 $cm^{-1}$ to 1489 $cm^{-1}$, and a wavenumber range from 1174 $cm^{-1}$ to 1286 $cm^{-1}$.

In some embodiments, at least one of the principal vibrational frequencies or components used in the chemometrics model for the host cell protein quantity corresponds to vibrational spectral information in a wavenumber range from 1500 $cm^{-1}$ to 1600 $cm^{-1}$, at least one of the principal vibrational frequencies or components corresponds to vibrational spectral information in a wavenumber range from 1600 $cm^{-1}$ to 1680 $cm^{-1}$, at least one of the principal vibrational frequencies or components corresponds to vibrational spectral information in a wavenumber range from 1414 $cm^{-1}$ to 1489 $cm^{-1}$, and at least one of the principal vibrational frequencies or components corresponds to vibrational spectral information in a wavenumber range from 1174 $cm^{-1}$ to 1286 $cm^{-1}$.

(iv) Charge Variant Distribution

In certain embodiments, the charge variant distribution for a process fluid in a biomanufacturing system can be used by controller 120 to adjust manufacturing process parameters. Accordingly, the methods disclosed herein can include obtaining and applying a chemometrics model to determine a charge variant distribution in a process fluid.

It has been determined that certain frequency ranges of principal vibrational frequencies or components for such chemometric models can yield chemometric models that more accurately predict values of the charge variant distribution. In some embodiments, for example, each of the principal vibrational frequencies or components used in the chemometrics model for the charge variant distribution can correspond to vibrational spectroscopic information in at least one of a wavenumber range from 1118 $cm^{-1}$ to 1500 $cm^{-1}$, a wavenumber range from 1120 $cm^{-1}$ to 1470 $cm^{-1}$, and a wavenumber range from 1187 $cm^{-1}$ to 1839 $cm^{-1}$.

In certain embodiments, at least one of the principal vibrational frequencies or components used in the chemometrics model for the charge variant distribution corresponds to vibrational spectroscopic information in a wavenumber range from 1118 $cm^{-1}$ to 1500 $cm^{-1}$, at least one of the principal vibrational frequencies or components corresponds to vibrational spectral information in a wavenumber range from 1120 $cm^{-1}$ to 1470 $cm^{-1}$, and at least one of the principal vibrational frequencies or components corresponds to vibrational spectral information in a wavenumber range from 1187 $cm^{-1}$ to 1839 $cm^{-1}$.

Alternatively, in some embodiments, the principal vibrational frequencies or components used in the chemometrics model for the charge variant distribution include a first group of at least three frequencies or components that correspond to vibrational spectral information in a wavenumber range from 1118 cm$^{-1}$ to 1500 cm$^{-1}$, a second group of at least three frequencies or components that correspond to vibrational spectral information in a wavenumber range from 1120 cm$^{-1}$ to 1470 cm$^{-1}$, and a third group of at least three frequencies or components that correspond to vibrational spectral information in a wavenumber range from 1187 cm$^{-1}$ to 1839 cm$^{-1}$. As discussed previously, among the principal vibrational frequencies or components, at least one or more may be common to at least two of the groups, or alternatively, none may be common to any two or more of the groups.

Chemometrics Models for Bioreactor-Based Analytes

Integrated continuous biomanufacturing systems typically implement continuous capture and post-capture processing (i.e., purification, polishing, and filtration) of drug substances and other reactor-derived products. In both continuous operation systems and more conventional batch-based bioreactor systems, methods for assessing bioreactor conditions and adjusting various process parameters are important to ensure high yields. Moreover, for large-scale manufacturing operations, and under relatively sensitive internal bioreactor conditions, it is desirable that methods for monitoring process parameters be highly automated, robust, and provide information that can be used to automatically adjust bioreactor conditions.

The specific cell lines and chemical media used under production conditions have been shown to significantly affect volumetric and specific productivity of a bioreactor. In particular, under suitable choice of cell line and bioreactor media, viable cell density (VCD) and volumetric productivity have been sustained for relatively long periods of time. FIGS. 18A-18D are graphs showing viable cell density (FIG. 18A), cell viability (FIG. 18B), harvest titer (FIG. 18C), and specific productivity (FIG. 18D) over a period of 45 days for a perfusion bioreactor. These data indicate that under the tested conditions, the reactor can be operated at a 1.5 RV/day perfusion rate with 100×10$^6$ viable cells/mL, with the viable cell density, cell viability, harvest titer, and specific productivity remaining relatively stable after the initial reactor conditions reach equilibrium.

Different VCD, pH conditions, and perfusion rates can adjust conditions within a bioreactor. Specifically, changes in any one or more of these operating parameters can change levels of various intermediates and medium components such as lactate, ammonium ions, glucose, and glutamine. Due to the importance of these intermediates in regulating production rates and affecting cell viability, values of many such quantities may be measured and adjusted relatively frequently to ensure that the bioreactor operates within a range of conditions that ensure stability and relatively high productivity. FIGS. 19A-19D are graphs showing how glucose concentrations (FIG. 19A), glutamine concentrations (FIG. 19B), lactate concentrations (FIG. 19C), and ammonium ion concentrations (FIG. 19D) vary under different cell density, pH, and perfusion conditions for a particular bioreactor producing a monoclonal antibody product.

Figure 20A:
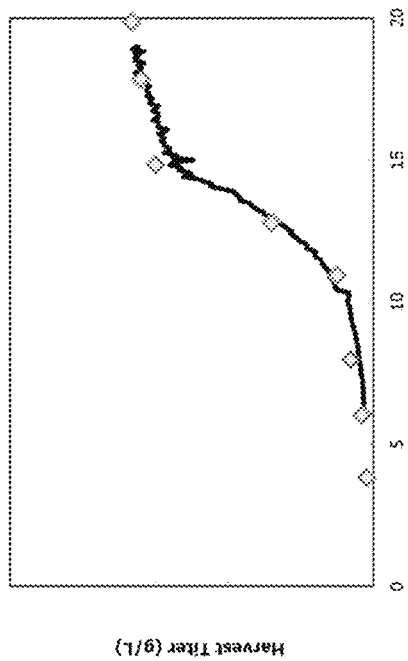
FIGS. 20A-20D are graphs showing daily measurements of glucose concentration, harvest titer, lactate concentration, and ammonium ion concentration for a bioreactor medium.
Figure 20B:
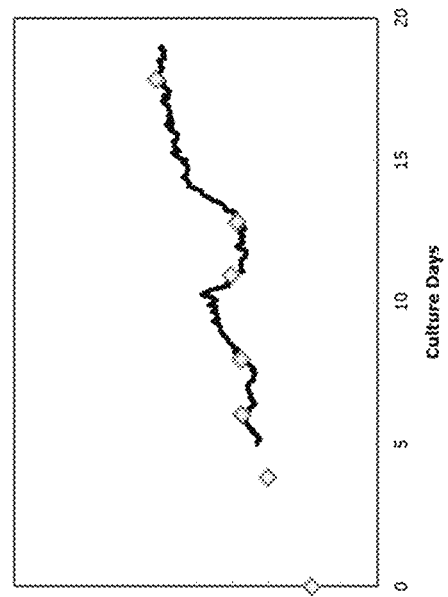
Figure 20C:
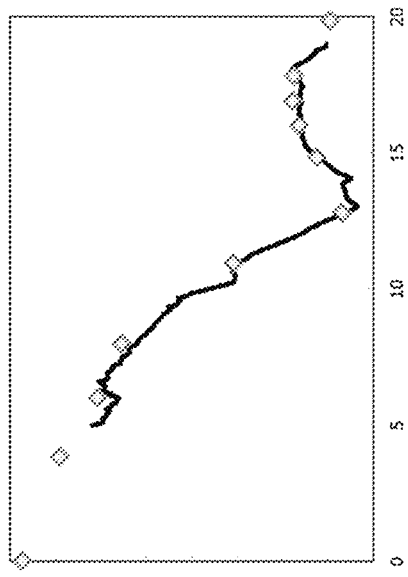
Figure 20D:
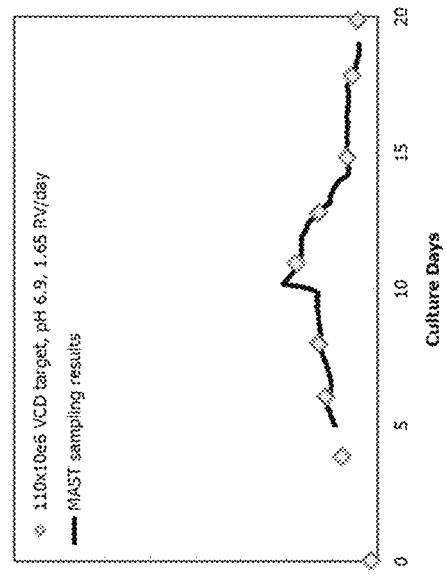
Figure 21A:
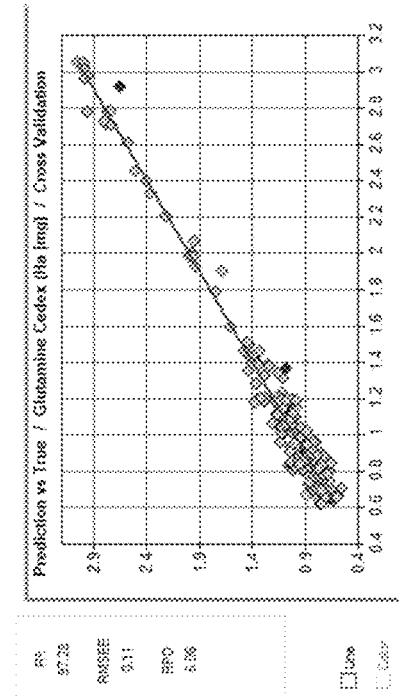
FIGS. 21A-21F are graphs showing measurements of glucose concentration, glutamine concentration, IgG concentration, lactate concentration, ammonium ion concentration, and osmolarity for a bioreactor medium determined from infrared spectral information.
Figure 21B:
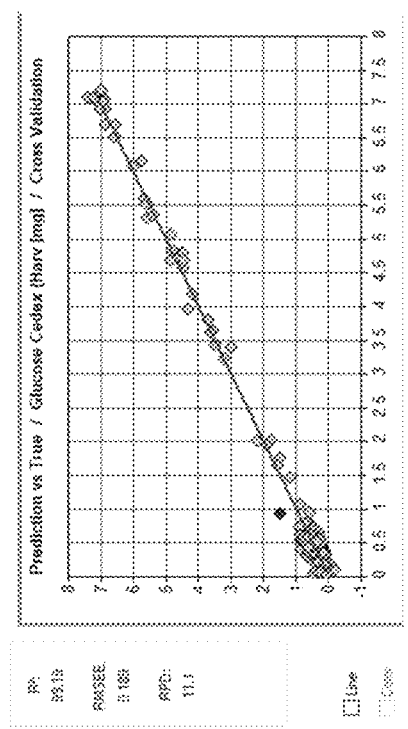
Figure 21C:
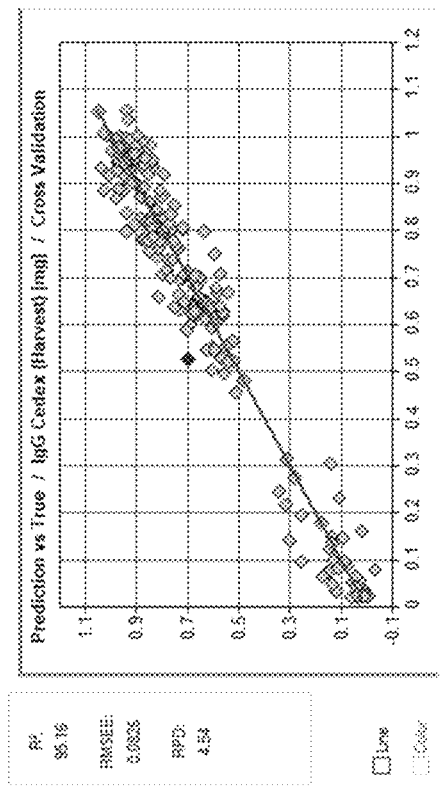
Figure 21E:
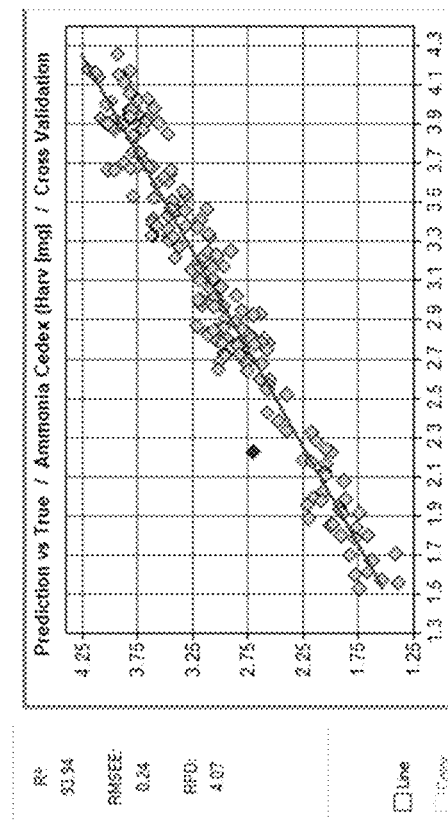
Figure 21D:
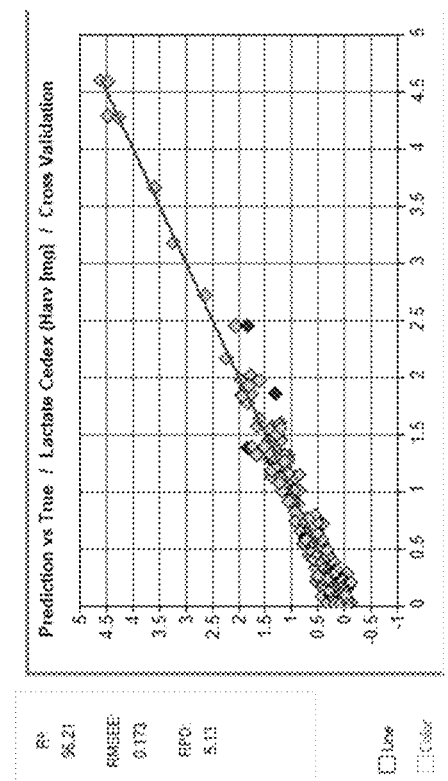
Figure 21F:
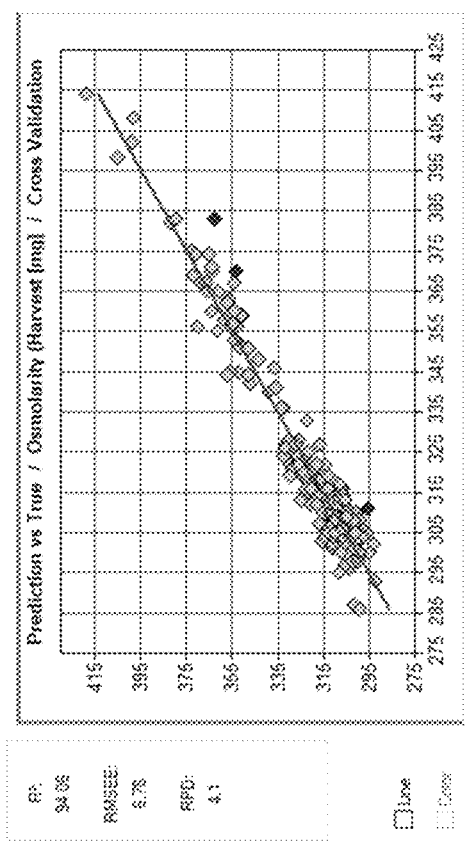

Due to the effect of these and other cell medium components and process intermediates on cell viability and productivity, measurement of values of these and other components provides important information about internal bioreactor processes, and can further provide data used to perform automated adjustment of bioreactor conditions that have deviated too far from specific target conditions. FIGS. 20A-20D are graphs showing daily at-line measurements of glucose concentration (FIG. 20A), harvest titer (FIG. 20B), lactate concentration (FIG. 20C), and ammonium ion concentration (FIG. 20D). The data in FIGS. 20A-20D were obtained in daily manual measurements, in which the bioreactor medium was sampled and separate analyses were conducted for each of the quantities in FIGS. 20A-20D.

Unfortunately, manual measurement of values of each of the foregoing quantities can be quite time-consuming, which limits the rate at which measurements can be made. The slower the rate at which measurements are made, the longer the delay before corrective adjustment of bioreactor conditions can occur. As such, product yields may be adversely affected if cell viability departs too significantly from ideal conditions. Further, frequency manual collection and processing of samples to measure values of these bioreactor medium components results in relatively high use of consumables associated with the sampling methods employed. Over time, the attendant cost of consumables can be significant.

The in-line infrared measurement techniques and chemometric methods discussed previously can be directly applied to the measurement of bioreactor medium-based components such as glucose, glutamine, lactate, and ammonium ions. The speed at which infrared spectral information can be obtained, and the non-invasive manner in which it can be obtained, make such measurements highly advantageous compared with manual sampling and analysis methods. Furthermore, chemometric methods with validated models allow values of multiple quantities to be extracted from a single set of infrared spectral information. As such, concentrations of glucose, glutamine, lactate, and ammonium ions (and other medium components) can each be derived from a single measured infrared spectrum analyzed with suitable chemometric models, which significantly reduces the number of spectral measurements that are performed, and in turn increases the rate at which bioreactor conditions can be adjusted in response to the measured values.

Integration and Adjustment of Biomanufacturing Systems

The measurement systems disclosed herein can be integrated with bio-manufacturing systems to provide feedback control to various components and steps in synthesis and purification processes for a variety of biological products. The measurement systems are typically implemented in-line between components of the manufacturing systems, so that flowing or stationary solutions can be analyzed in real time with no sampling or diversion. The measurement systems can also be used more conventionally with samples extracted from reaction vessels, holding tanks, or chromatography columns prior to performing infrared spectroscopic measurements.

Integrated and fully continuous processes for manufacturing therapeutic protein drugs and other substances can include, e.g., providing a liquid culture medium containing a recombinant therapeutic protein that is substantially free of cells, then feeding the liquid culture medium into a first multi-column chromatography system (MCCS1). The next step involves capturing the recombinant therapeutic protein in the liquid culture medium using the MCCS1, and then continuously feeding the eluate of the MCCS1 containing the recombinant therapeutic protein into a second multi-column chromatography system (MCCS2), and purifying and polishing the protein using the MCCS2. The resulting eluate from the MCCS2 is considered a therapeutic protein drug substance. The processes are integrated and can run continuously from the liquid culture medium to the eluate from the MCCS2 that is the therapeutic protein drug substance.

Bio-manufacturing systems are typically used to perform the above processes. For example, such systems can include a MCCS1 that includes an inlet and a MCCS2 that includes an outlet. In these systems, the first and second MCCSs are in fluid communication with each other. The systems are also configured such that fluid can be passed into the inlet, through the first and second MCCSs, and exit the manufacturing system through the outlet.

Such systems can provide for continuous and time-efficient production of a therapeutic drug substance from a liquid culture medium. For example, the elapsed time between feeding a fluid (e.g., a liquid culture medium) containing a therapeutic protein into the first MCCS and eluting a therapeutic protein drug substance (containing the therapeutic protein) from the outlet of the second MCCS can be, e.g., between about 4 hours and about 48 hours.

Figure 10:
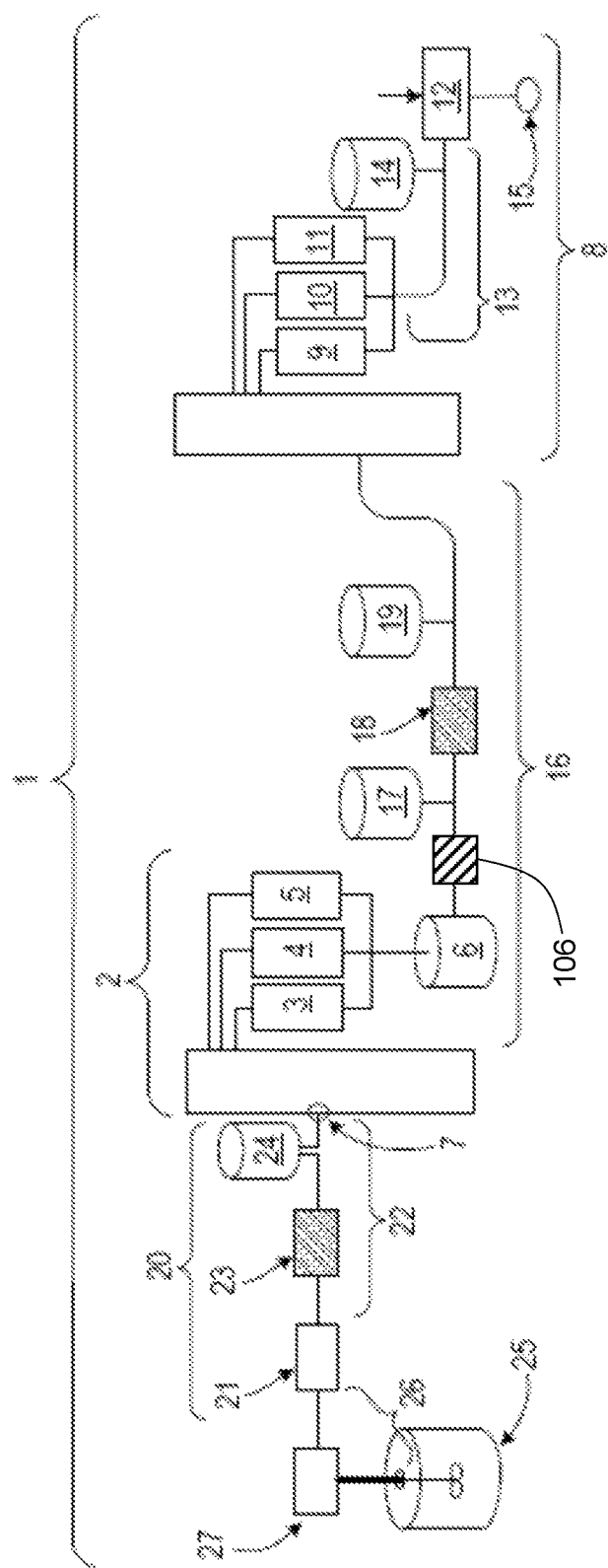
FIG. 10 is a schematic diagram showing an example of a bio-manufacturing system.

FIG. 10 is a schematic diagram showing an example of a bio-manufacturing system. System 1 includes a first MCCS, i.e., a four-column Periodic Counter-Current Chromatography System (PCCS) 2, where three of the four columns 3, 4, and 5 in four-column PCCS 2 perform the unit operation of capturing the recombinant therapeutic protein from a fluid containing the recombinant therapeutic protein (e.g., liquid culture medium that is substantially free of mammalian cells), and one of the columns 6 in PCCS 2 performs the unit operation of inactivating viruses present in the eluate from columns 3, 4, and 5 in PCCS 2 containing the recombinant therapeutic protein. Columns 3, 4, and 5 can contain a resin that utilizes a Protein A-binding capture mechanism. Column 6 is capable of holding a fluid at a pH of about 3.75 for about 1 hour. PCCS 1 also has an inlet 7. Inlet 7 can be, e.g., an orifice that accepts entry of a fluid into PCCS 1.

System 1 also includes a second MCCS that is a PCCS 8 that includes three chromatography columns 9, 10, and 11 and one chromatographic membrane 12. Columns 9, 10, and 11 in PCCS 8 can contain a cationic exchange resin. Chromatographic membrane 12 in PCCS 8 can contain a cationic exchange resin. PCCS 8 also has a fluid conduit 13 disposed between columns 9, 10, and 11 in PCCS 8 and chromatographic membrane 12 in PCCS 8. PCCS 8 also has an in-line buffer adjustment reservoir 14 that is in fluid communication with fluid conduit 13, and is configured such that buffer contained within in-line buffer adjustment reservoir 14 is introduced into the fluid present in fluid conduit 13. PCCS 8 also includes an outlet 15. Outlet 15 can be, e.g., an orifice that allows exit of the fluid from PCCS 8.

System 1 can further include a fluid conduit 16 disposed between PCCS 2 and PCCS 8. System 1 can also include an in-line buffer adjustment reservoir 17 in fluid communication with fluid conduit 16 configured such that the buffer contained within in-line buffer adjustment reservoir 17 can be introduced into the fluid present in fluid conduit 16. System 1 can also include a filter 18 disposed in fluid conduit 16 to filter the fluid present in fluid conduit 16. System 1 can also include a break tank 19 disposed in fluid conduit 16 and configured to hold any fluid in fluid conduit 16 that cannot be readily fed into PCCS 8.

System 1 can further include a pump system 20 that is in fluid communication with inlet 7. Pump system 20 can include a pump 21 for pushing fluid into inlet 7. System 1 can also include a fluid conduit 22 disposed between pump 21 and inlet 7. System 1 can also include a filter 23 disposed in fluid conduit 22 to filter the fluid (e.g., liquid culture medium) present in fluid conduit 22. System 1 can also include a break tank 24 disposed in fluid conduit 22 configured such that break tank 24 is in fluid communication with fluid conduit 22 and is capable of storing any fluid present in fluid conduit 22 that is not able to enter inlet 7.

System 1 can also include a bioreactor 25 and a fluid conduit 26 disposed between bioreactor 25 and pump 21. A filtration system 27 may be disposed in fluid conduit 26 to filter (e.g., remove cells from) a liquid culture medium present in fluid conduit 26.

The first MCCS (PCCS 2) includes an inlet through which fluid (e.g., a liquid culture medium that is substantially free of cells) can be passed into the first MCCS. The inlet can be any structure known in the art for such purposes. It can include, e.g., a threading, ribbing, or a seal that allows for a fluid conduit to be inserted, such that after insertion of the fluid conduit into the inlet, fluid will enter the first MCCS through the inlet without significant seepage of fluid out of the inlet.

The first MCCS includes at least two chromatography columns, at least two chromatographic membranes, or at least one chromatography column and at least one chromatographic membrane, and an inlet. For example, the first MCCS can include a total of four chromatography columns, or three chromatography columns and one chromatographic membrane, or any of the other exemplary MCCSs described herein, or have one or more of any of the exemplary features of a MCCS (in any combination) described herein.

The chromatography column(s) and/or the chromatographic membrane(s) present in the first MCCS can contain one or more of a variety of resins. For example, the resin contained in one or more of the chromatography column(s) and/or chromatographic membrane(s) present in the first MCCS can be a resin that utilizes a capture mechanism (e.g., Protein A-binding capture mechanism, protein G-binding capture mechanism, antibody- or antibody fragment-binding capture mechanism, substrate-binding capture mechanism, cofactor-binding capture mechanism, an aptamer-binding capture mechanism, and/or a tag-binding capture mechanism) The resin contained in one or more of the chromatography column(s) and/or chromatographic membrane(s) of the first MCCS can be a cation exchange resin, an anion exchange resin, a molecular sieve resin, or a hydrophobic interaction resin, or any combination thereof. Additional examples of resins that can be used to purify a recombinant therapeutic protein are known in the art, and can be contained in one or more of the chromatography column(s) and/or chromatographic membrane(s) present in the first MCCS. The chromatography column(s) and/or chromatography membranes present in the first MCCS can contain the same and/or different resins (e.g., any of the resins described herein or known in the art for use in recombinant protein purification).

The two or more chromatography column(s) and/or chromatographic resin(s) present in the first MCCS can perform one or more unit operations (e.g., capturing a recombinant therapeutic protein, purifying a recombinant therapeutic protein, polishing a recombinant therapeutic protein, inactivating viruses, adjusting the ionic concentration and/or pH of a fluid containing the recombinant therapeutic protein, or filtering a fluid containing a recombinant therapeutic protein). In non-limiting examples, the first MCCS can perform the unit operations of capturing a recombinant therapeutic protein from a fluid (e.g., a liquid culture medium) and inactivating viruses present in the fluid containing the recombinant therapeutic protein. The first MCCS can perform any combination of two of more unit operations described herein or known in the art.

The chromatography column(s) and/or chromatographic membrane(s) present in the first MCCS can be connected or moved with respect to each other by a switching mechanism (e.g., a column-switching mechanism) The first MCCS can also include one or more (e.g., two, three, four, or five) pumps (e.g., automated, e.g., automated peristaltic pumps).

The column-switching events can be triggered by the detection of a level of recombinant therapeutic protein in the fluid passing through the first MCCS (e.g., the input into and/or eluate from one or more of the chromatography column(s) and/or chromatographic membranes in the first MCCS), a specific volume of liquid (e.g., buffer), or specific time elapsed. Column switching generally means a mechanism by which at least two different chromatography columns and/or chromatographic membranes in an MCCS (e.g., two or more different chromatography columns and/or chromatographic membranes present in an MCCS (e.g., the first or second MCCS)) are allowed to pass through a different step (e.g., equilibration, loading, eluting, or washing) at substantially the same time during at least part of the process.

PCCS 2 that is the first MCCS can include four chromatography columns, where the first three columns perform the unit operation of capturing a recombinant therapeutic protein from a fluid (e.g., a liquid culture medium), and the fourth column of the PCCS performs the unit operation of inactivating viruses in the fluid containing the recombinant therapeutic protein. A PCCS that is the first MCCS can utilize a column-switching mechanism. The PCC system can utilize a modified ÄKTA system (GE Healthcare, Piscataway, NJ) capable of running up to, e.g., four, five, six, seven, or eight columns, or more.

Column switching events can be triggered by detection of a concentration of a particular protein or other substance in a fluid eluting from one of the columns of PCCS 2 or PCCS 8, flowing through a filter in the MCCS, contained in a break tank of the MCCS, or flowing through a conduit in the MCCS (e.g., between MCCS 1 and MCCS 2). The measurement systems disclosed herein can be used to measure concentrations of such proteins, and to transmit the concentration information to a controller in system 1 that initiates events such as column switching, filtering, and fluid transport in system 1.

The first MCCS can be equipped with: one or more (e.g., two, three, four, five, six, seven, eight, nine, or ten) measurement systems configured to obtain infrared spectroscopic information for process fluids (e.g., system 100), one or more (e.g., two, three, four, five, six, seven, eight, nine, or ten) valves, one or more (e.g., two, three, four, five, six, seven, eight, nine, or ten) pH meters, and/or one or more (e.g., two, three, four, five, six, seven, eight, nine, or ten) conductivity meters. The first MCCS can also be equipped with a controller executing an operating system that utilizes software (e.g., Unicorn-based software, GE Healthcare, Piscataway, NJ, or other software implementing similar functionality) for determining when a column-switching should occur (e.g., based upon concentration information derived from infrared spectroscopic measurements, volume of liquid, or elapsed time) and affecting (triggering) the column-switching events. The measurement systems can be placed optionally at the inlet of one or more (e.g., two, three, four, five, six, seven, eight, nine, or ten) of the chromatography column(s) and/or chromatographic membrane(s) in the first MCCS, and/or at the outlet of one or more of the chromatography column(s) and/or chromatography membrane(s) in the first MCCS.

The first MCCS can further include one or more (e.g., two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) in-line buffer adjustment reservoir(s) and/or a buffer reservoir(s). In other examples, the first MCCS can include one or more (e.g., two, three, four, five, or six) break tanks that can hold fluid that cannot readily pass into one or more of the chromatography columns and/or chromatographic membranes in the first MCCS. The systems described herein can contain one or more break tanks (e.g., a break tank described herein) in the first and/or second MCCS. Other examples of the systems described herein do not include a break tank in the first MCCS or the second MCCS, or do not include a break tank in the entire system. Other examples of the systems include a maximum of one, two, three, four, or five break tank(s) in the entire system.

In some embodiments, the first MCCS can include a viral inactivation device. For example, referring to FIG. 10, in certain embodiments the first MCCS includes viral inactivation device 6 (i.e., in place of column 6 described above). Viral inactivation device 6 is configured to inactivate viruses and viral vectors used in biomanufacturing processes. In some embodiments, for example, viral inactivation device 6 includes a mixing vessel. Alternatively, in certain embodiments for example, device 6 includes a plug flow inactivation system. Each of these examples of viral inactivation devices helps to eliminate active viruses and viral vectors from process fluids in the first MCCS.

The second MCCS includes at least two chromatography columns, at least two chromatographic membranes, or at least one chromatography column(s) and at least one chromatographic membrane(s), and an outlet. For example, the second MCCS can include a total of four chromatography columns, three chromatography columns and one chromatographic membrane, or any of the other exemplary MCCSs described herein, or can have one or more of any of the exemplary features of an MCCS (in any combination) described herein. The chromatography column(s) and/or the chromatographic membrane(s) present in the second MCCS can have one or more of: any of the shapes, sizes, volumes (bed volumes), and/or unit operations described herein. The resin contained in one or more of the chromatography column(s) and/or chromatographic membrane(s) present in the second MCCS can be a resin that utilizes a capture mechanism (e.g., Protein A-binding capture mechanism, Protein G-binding capture mechanism, antibody- or antibody fragment-binding capture mechanism, substrate-binding capture mechanism, cofactor-binding capture mechanism, tag-binding capture mechanism, and/or aptamer-binding capture mechanism) Useful resins include, e.g., a cation exchange resin, an anion exchange resin, a molecular sieve resin, and a hydrophobic interaction resin. The chromatography column(s) and/or chromatography membranes present in the second MCCS can contain the same and/or different resins (e.g., any of the resins described herein or known in the art for use in recombinant protein purification).

The chromatography column(s) and/or chromatographic membrane(s) present in the second MCCS can perform one or more unit operations (e.g., any of the unit operations described herein or any combination of the unit operations described herein). In non-limiting examples, the second MCCS can perform the unit operations of purifying a recombinant therapeutic protein from a fluid and polishing the recombinant therapeutic protein present in the fluid containing the recombinant therapeutic protein. In other non-limiting examples, the second MCCS can perform the unit operations of purifying a recombinant therapeutic protein present in a fluid, polishing a recombinant therapeutic protein present in a fluid, and filtering a fluid containing a recombinant therapeutic protein. In another example, the second MCCS can perform the unit operations of purifying a recombinant therapeutic protein present in a fluid, polishing a recombinant therapeutic protein present in a fluid, filtering a fluid containing a recombinant therapeutic protein, and adjusting the ionic concentration and/or pH of a fluid containing a recombinant therapeutic protein. The second MCCS can perform any combination of two of more unit operations described herein or known in the art.

The second MCCS can also include one or more (e.g., two, three, four, or five) pumps (e.g., automated, e.g., automated peristaltic pumps).

The chromatography column(s) and/or chromatographic membrane(s) present in the second MCCS can be connected or moved with respect to each other by a switching mechanism (e.g., a column-switching mechanism) The column-switching events can be triggered by the detection of a level of recombinant therapeutic protein or other substance via infrared spectroscopic measurements and analysis thereof using chemometric models, as discussed above, to determine the level of recombinant therapeutic protein in the fluid passing through the second MCCS (e.g., the input into and/or eluate from one or more of the chromatography column(s) and/or chromatographic membranes in the second MCCS), a specific volume of liquid (e.g., buffer), or specific time elapsed.

The PCCS 8 that forms the second MCCS can contain three columns that perform the unit operation of purifying a recombinant therapeutic protein from a fluid, and a chromatographic membrane that performs the unit operation of polishing a recombinant therapeutic protein present in a fluid. For example, the three columns that perform the unit operation of purifying a recombinant therapeutic protein from a fluid can contain, e.g., a cationic exchange resin, and the chromatographic membrane that performs the unit operation of polishing can contain a cationic exchange resin. A PCCS that is the second MCCS can utilize a column-switching mechanism. For example, the PCCS can utilize a modified ÄKTA system (GE Healthcare, Piscataway, NJ) capable of running up to, e.g., four, five, six, seven, or eight columns, or more.

Similar to the first MCCS, the second MCCS can also be equipped with: one or more (e.g., two, three, four, five, six, seven, eight, nine, or ten) infrared spectroscopic measurement systems, one or more (e.g., two, three, four, five, six, seven, eight, nine, or ten) valves, one or more (e.g., two, three, four, five, six, seven, eight, nine, or ten) pH meters, and/or one or more (e.g., two, three, four, five, six, seven, eight, nine, or ten) conductivity meters. The one or more measurement systems transmit concentration information for the protein or other substance in the fluid that is measured to a controller that uses the concentration information to determine whether to trigger a column switching event. The second MCCS can be equipped with an operating system, executed by the controller that receives the concentration information, that utilizes software (e.g., Unicorn-based software, GE Healthcare, Piscataway, NJ) for determining when a column-switching event should occur (e.g., based upon infrared spectroscopic measurements, volume of liquid, or elapsed time) and initiating the column-switching events. In the examples where the second MCCS includes one or more infrared spectroscopic measurement systems, the measurement systems can be placed optionally at the inlet of one or more (e.g., two, three, four, five, six, seven, eight, nine, or ten) of the chromatography column(s) and/or chromatographic membrane(s) in the second MCCS, and/or at the outlet of one or more of the chromatography column(s) and/or chromatography membrane(s) in the second MCCS.

The second MCCS can further include one or more (e.g., two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) in-line buffer adjustment reservoir(s) and/or a buffer reservoir(s). In other examples, the second MCCS can include one or more (e.g., two, three, four, five, or six) break tanks (e.g., any of the break tanks described herein) that can hold fluid that cannot readily pass into one or more of the chromatography columns and/or chromatographic membranes in the second MCCS.

The second MCCS includes an outlet through which the therapeutic protein drug substance can exit the system. The outlet can include, e.g., a threading, ribbing, or a seal that allows for a fluid conduit to be inserted or a vial designed to contain or store the therapeutic protein drug substance. An outlet can contain a surface that can be used to seal a sterile vial or other such storage container onto the outlet in order to allow the recombinant protein drug product to flow directly into the sterile vial or storage container.

One or more infrared spectroscopic measurement systems, as disclosed herein, can also be positioned to measure the concentration of the protein drug substance (or another substance) flowing out of the outlet. This information can be transmitted to the MCCS controller, which can determine a purity of the substance based on the information.

The systems described herein can also include a fluid conduit that is disposed between the first MCCS and the second MCCS. One or more infrared spectroscopic measurement systems can be disposed along the fluid conduit to determine information (e.g., concentration information) about fluids held within (e.g., flowing through) the conduit. This information can be communicated to a MCCS controller which, as discussed above, can determine whether to initiate a column-switching event based on the information.

Any of the fluid conduits described herein can be, e.g., a tube that is made of, e.g., polyethylene, polycarbonate, or plastic. The fluid conduit disposed between the first MCCS and the second MCCS can further include one of more of the following in any combination: one or more in-line buffer adjustment reservoirs that are in fluid communication with the fluid conduit and are positioned such that the buffer stored within the in-line buffer adjustment reservoir(s) is added to the fluid present in the fluid conduit; a break tank (e.g., any of the break tank(s) described herein) that is in fluid communication with the fluid conduit and is positioned such that it can hold any excess fluid present in the fluid conduit that is unable to readily feed into the second MCCS; and one or more filters that are disposed in the fluid conduit such that they are capable of filtering (e.g., removing bacteria) the fluid present in the fluid conduit. Any of the in-line buffer adjustment reservoirs can contain, e.g., a volume of between about 0.5 L to 50 L of buffer (e.g., at a temperature at or below 50° C., 37° C., 25° C., 15° C., or 10° C.).

The systems described herein can optionally include a fluid conduit disposed between the final chromatography column or chromatographic membrane in the second MCCS and the outlet. The systems described herein can further include one or more filters in fluid connection with the fluid conduit disposed between the final chromatography column or chromatographic membrane in the second MCCS and the outlet, such that the filter can remove, e.g., precipitated material, particulate matter, or bacteria from the fluid present in the fluid conduit disposed between the final chromatography column or chromatographic membrane in the second MCCS and the outlet.

Some examples of the systems provided herein also include a bioreactor that is in fluid connectivity with the inlet of the first MCCS. Any of the exemplary bioreactors described herein or known in the art can be used in the present systems.

Some examples of the systems provided herein also include a pump system. A pump system can include one or more the following: one or more (e.g., two, three, four, five, six, seven, eight, nine, or ten) pumps (e.g., any of the pumps described herein or known in the art), one or more (e.g., two, three, four, or five) filters (e.g., any of the filters described herein or known in the art), one or more (e.g., two, three, four, five, six, seven, eight, nine, or ten) UV detectors, and one or more (e.g., two, three, four, or five) break tanks (e.g., any of the break tanks described herein). Some examples of the systems provided herein further include a fluid conduit disposed between the pump and the inlet of the first MCCS (e.g., any of the exemplary fluid conduits described herein or known in the art). In some examples, this particular fluid conduit can include one or more (e.g., two, three, or four) pumps (e.g., any of the pumps described herein or known in the art) and/or one or more (e.g., two, three, or four) break tanks (e.g., any of the exemplary break tanks described herein), where these pump(s) and/or break tank(s) are in fluid connection with the fluid present in the fluid conduit.

Some examples of the systems described herein further include a further fluid conduit connected to the fluid conduit between the pump and the inlet, where one end of the further fluid conduit is fluidly connected to a bioreactor and the other end is fluidly connected to the fluid conduit between the pump and the inlet. This further fluid conduit can include a filter that is capable of removing cells from the liquid culture medium removed from the bioreactor (e.g., ATF cell retention system).

The foregoing bio-manufacturing systems allow for the continuous production of a therapeutic protein drug substance. For example, the systems provided herein allow for a percentage yield of recombinant therapeutic protein (from a starting material, e.g., a starting liquid culture medium) of greater than about 70%, greater than about 80%, greater than about 82%, greater than about 84%, greater than about 86%, greater than about 88%, greater than about 90%, greater than about 92%, greater than about 94%, greater than about 96%, or greater than about 98%. The systems described herein can also result in a percentage yield of recombinant therapeutic protein (from a starting material, e.g., a starting liquid culture medium) of between about 80% to about 90%, between about 82% to about 90%, between about 84% to about 90%, between about 84% to about 88%, between about 84% to about 94%, between about 82% to about 92%, or between about 85% to about 95%.

The systems described herein can also result in the production of a therapeutic protein drug substance that contains a concentration of recombinant therapeutic protein that is greater than about 1.0 mg/mL, e.g., greater than about 15 mg/mL, greater than about 20 mg/mL, greater than about 25 mg/mL, greater than about 30 mg/mL, greater than about 35 mg/mL, greater than about 40 mg/mL, greater than about 45 mg/mL, greater than about 50 mg/mL, greater than about 55 mg/mL, greater than about 60 mg/mL, greater than about 65 mg/mL, greater than about 70 mg/mL, greater than about 75 mg/mL, greater than about 80 mg/mL, greater than about 85 mg/mL, greater than about 90 mg/mL, greater than about 100 mg/mL, greater than about 125 mg/mL, or greater than about 150 mg/mL.

As discussed above, in some embodiments, the first and/or second MCCS can be a Periodic Counter-Current Chromatography System (PCCS). A PCCS can, e.g., include two or more chromatography columns (e.g., three columns or four columns) that are switched in order to allow for the continuous elution of recombinant therapeutic protein from the two or more chromatography columns. A PCCS can include two or more chromatography columns, two or more chromatographic membranes, or at least one chromatographic column and at least one chromatographic membrane. A column operation generally consists of the load, wash, elute, and regeneration steps. In PCCSs, multiple columns are used to run the same steps discretely and continuously in a cyclic fashion. Since the columns are operated in series, the flow through and wash from one column is captured by another column. This unique feature of PCCSs allows for loading of the resin close to its static binding capacity instead of to the dynamic binding capacity, as is typical during batch mode chromatography.

Figure 11:
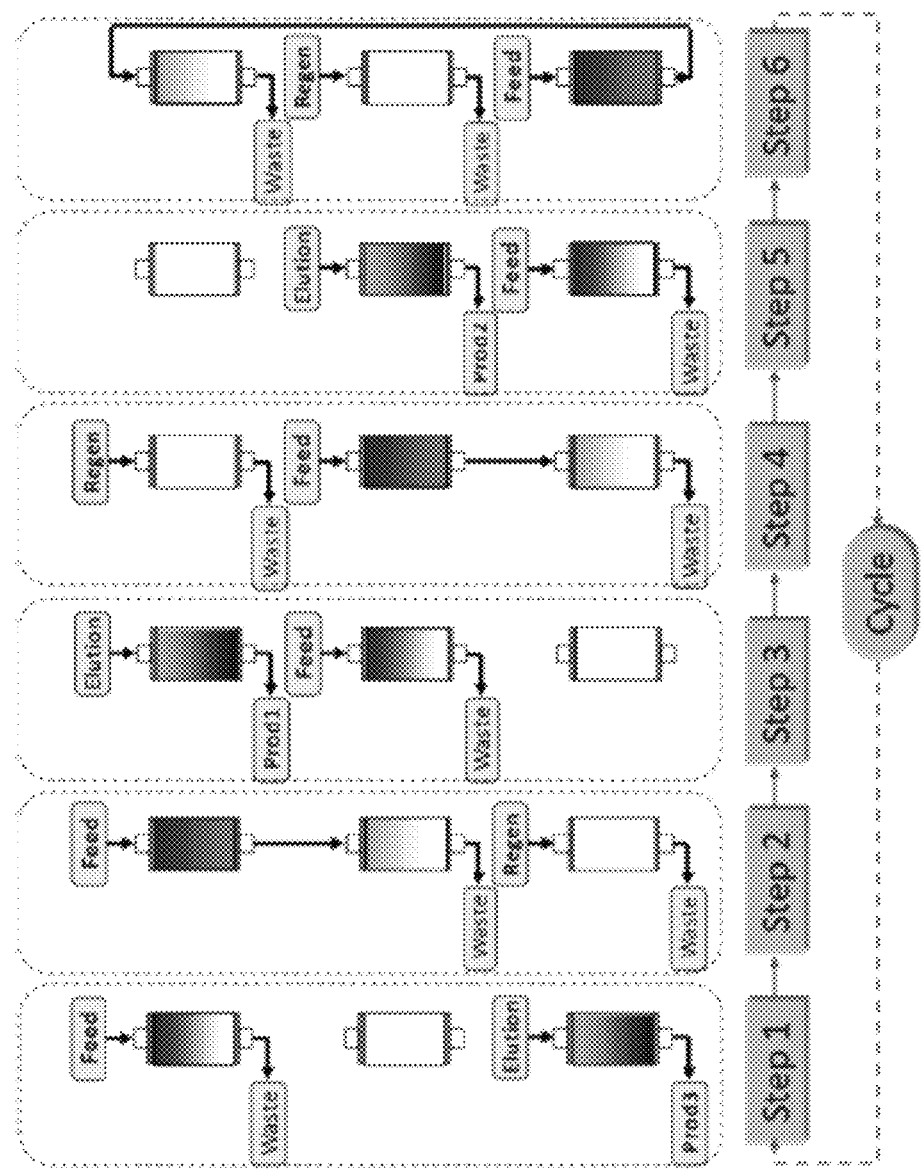
FIG. 11 is a schematic diagram showing an example of a three-column switching technique in a periodic counter-current chromatography system.

An example of the three column-switching technique used in a PCCS containing three columns is shown in FIG. 11. A cycle is defined as three complete column operations resulting in an elution pool from each of the three columns used in the column-switching technique. Once all the steps in the cycle are completed, the cycle is re-started. As a result of the continuous cycling and elution, fluid entering a PCCS is processed continuously, while recombinant therapeutic protein elution from each column is discrete and periodic.

To advance from one step to another in a PCCS cycle, such as the exemplary cycle shown in FIG. 11, a column-switching strategy is employed. The column switching method employs two automated switching operations per column in the three-columns in the exemplary PCCS system shown in FIG. 11, the first of which is related to the initial product breakthrough, while the second coincides with column saturation. The determination of when the column switching operations should take place is based on information about recombinant therapeutic protein concentrations in the eluate from each chromatography column in the PCCS.

As discussed above, the infrared spectroscopic measurement systems disclosed herein can be used to determine concentrations of recombinant therapeutic proteins in eluate from PCCS columns. The concentration information—which functions as a feedback control for the bio-manufacturing system—is transmitted to the MCCS controller, which initiates column switching after determining that a switch is warranted.

As an example, during column loading, the PCC control system can determine a baseline concentration of a therapeutic protein substance eluting from the column (which is typically zero concentration) using the infrared spectroscopic measurement systems discussed above. During active elution, as the protein substance breaks through, there is an increase (e.g., above the baseline concentration) in the measured protein concentration. The system continues to monitor the increasing protein concentration, and when the concentration reaches a pre-determined threshold value, the flow-through from column 1 is directed onto column 2 instead of to the waste. Nominally, this occurs at a time $t_1$.

As the feed continues into column 1, column 1 eventually becomes nearly saturated with the protein product. At this point, the measured concentration of protein in the eluate has reached another pre-determined value, which occurs at a time $t_2$. At this point, the MCCS controller switches the inlet feed to column 2.

The above column-switching strategy allows for the uniform loading of the columns irrespective of the feed product concentration and the capacity. Similar switches of the columns based on the level of recombinant protein detected in the eluate from each column can be implemented. Column switches can also be based on elapsed time or the amount of fluid (e.g., buffer) passed through the one or more chromatography column(s) and/or chromatographic membranes in the first or second MCCS.

In addition to providing feedback information to control column switching events, the measurement systems disclosed herein can also provide feedback information for the adjustment of various other bio-manufacturing steps and operating parameters. One example of such adjustments is the controlled adjustment of buffer concentrations at various stages of the bio-manufacturing processes.

In general, one or more (e.g., three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) different types of buffer can be employed during the use of the two or more MCCSs in any of the processes described herein. As is known in the art, the one or more types of buffer used in the two or more MCCSs used in the processes described herein will depend on the resin present in the chromatography column(s) and/or the chromatographic membrane(s) of the two or more MCCSs (e.g., the first and second MCCSs), the recombinant therapeutic protein, and unit operation (e.g., any of the exemplary unit operations described herein) performed by the specific chromatography column(s) and/or chromatography membranes of the two or more MCCSs. The volume and type of buffer employed during the use of the two or more MCCSs in any of the processes described herein can also be determined by one skilled in the art (e.g., discussed in more detail below). For example, the volume and type(s) of buffer employed during the use of the two or more MCCSs in any of the processes described herein can be chosen in order to optimize one or more of the following in the recombinant protein drug product: the overall yield of recombinant therapeutic protein, the activity of the recombinant therapeutic protein, the level of purity of the recombinant therapeutic protein, and the removal of biological contaminants from a fluid containing the recombinant therapeutic protein (e.g., absence of active viruses, mycobacteria, yeast, bacteria, or mammalian cells).

The unit operations of adjusting the ionic concentration and/or pH of a fluid containing the recombinant therapeutic protein can be performed using a MCCS (e.g., the first and/or second MCCS) that includes and utilizes a buffer adjustment reservoir (e.g., an in-line buffer adjustment reservoir) that adds a new or additional buffer solution into a fluid that contains the recombinant therapeutic protein (e.g., between columns within a single MCCS, or after the last column in a penultimate MCCS (e.g., the first MCCS) and before the fluid containing the recombinant therapeutic protein is fed into the first column of the next MCCS (e.g., the second MCCS). The in-line buffer adjustment reservoir can be any size (e.g., greater than 100 mL) and can contain any buffered solution (e.g., a buffered solution that has one or more of: an increased or decreased pH as compared to the fluid containing the recombinant therapeutic protein, an increased or decreased ionic (e.g., salt) concentration compared to the fluid containing the recombinant therapeutic protein, and/or an increased or decreased concentration of an agent that competes with the recombinant therapeutic protein for binding to resin present in at least one chromatographic column or at least one chromatographic membrane in an MCCS (e.g., the first or the second MCCS)).

In some embodiments, determination by the MCCS controller of the amount of buffer solution to add to process fluid is based on concentration information about a component of the process fluid derived from infrared spectroscopic measurements performed as discussed previously. For example, the solute for purposes of such measurements can be a buffer solution component or a component of the process fluid for which the concentration is related to the fluid buffer composition, the pH of the process fluid, and/or the ionic strength of the process fluid. Measurement of the concentration information for the component is provided as feedback information to the MCCS controller, which uses the feedback information to determine when and what quantity of one or more buffer solutions to discharge into the process fluid. Infrared spectroscopic measurement systems can generally be positioned at any location in the bio-manufacturing system for purposes of measuring process fluids to provide buffer-related feedback information to the MCCS controller.

In certain embodiments, antibody concentration information for a process fluid can be used to control a rate at which cell cultures are introduced into a bioreactor. In particular, by determining the antibody concentration value in a process fluid harvested from the bioreactor, the MCCS controller can adjust the bleed rate of the cell culture into the bioreactor. Adjustment in this manner allows control of the volumetric productivity derived from cell density and specific productivity of the bioreactor. For a fixed perfusion rate, such adjustments permit control of the antibody concentration in the process fluid such that MCCS1 would receive an approximately constant amount of product per unit time. In other words, adjustments of this nature can be used to ensure that the rate of product generation within the bioreactor remains approximately constant over a particular time period.

In some embodiments, determination of certain quality attributes associated with process fluids can be used by the MCCS controller to determine whether a biomanufacturing system is operating within an acceptable range of parameters, or whether during operation, the system is outside one or more acceptable parameter ranges.

For each of one or more quality attributes, a range of acceptable values can be established through calibration procedures. These ranges effectively establish operating conditions for the system under which biological products are generated at acceptable rates and levels of purity, while the yields of by-products and other undesirable species are at acceptably low levels. When the system operates outside of one or more of the ranges, product yields and/or purity may be reduced, rates/quantities of production of undesirable species may be increased, reagent consumption rates may be increased, and/or other undesirable effects or conditions may result.

Quality attributes determined for process fluids at one or more locations within the system can be used to ensure that the system operates within acceptable ranges of these operating parameters. If the determined values of one or more of the quality attributes fall outside the established acceptable ranges, the MCCS controller identifies that a potential fault condition exists.

To address a fault condition, the MCCS controller (or another system controller connected to the MCCS controller) can adjust any of the operating parameters of the biomanufacturing system to modify its operation, thereby also adjusting values of the quality attributes such that they fall within acceptable ranges. Corrective actions of this nature ensure that, based on feedback provided by the determined values of the quality attributes, the system can be actively maintained within an established set or range of operating conditions.

In certain embodiments, if the MCCS controller (or another system controller connected to the MCCS controller) determines that the system is too far out of range from its acceptable range of operating conditions such that returning the system to an acceptable range of conditions would be difficult or even impossible, or would result in other undesirable consequences, the controller can transmit control signals to the bioreactor to discontinue production and discharge its contents to waste. In such a case, effective corrective action is impractical or impossible—the production process has deviated too far from the acceptable range of operating conditions for the system. By simply discharging the contents of the bioreactor, the system can save considerable time by restarting the production process, rather than attempting to adjust an ongoing production process that may have deviated irretrievably from an acceptable range of conditions.

Further, feedback can be provided to the MCCS controller (or to another system controller) based on measured values of one or more bioreactor medium components (such as glucose concentration, glutamine concentration, lactate concentration, and ammonium ion concentration), which can then be used to adjust reactor conditions to ensure that cell viability, product yields, and other performance metrics are maintained within target ranges. Any one or more process parameters can be adjusted by the controller based on values of the bioreactor medium components in a manner similar to adjustments made based on product quality attributes and values of other measured quantities.

EXAMPLES

The following examples are provided to further illustrate various aspects of the foregoing disclosure, but are not intended to otherwise limit any features of the claims, or limit any aspects of the embodiments unless expressly stated.

To evaluate the methods and systems disclosed herein, FTIR spectroscopy using the ATR geometry and partial least-squares multivariate data analysis were used to develop chemometric models for rapid and accurate determination of multiple process physical and chemical attributes using a single set (Multi Attribute Product Quality (MAP-Q) of vibrational spectroscopic information. Protein A purified samples from multiple harvest days of antibody drug candidate-X were analyzed for their concentration, aggregation, charge variant distribution, and host cell protein (HCP) content using offline reference assays (Chromatography and ELISA) and the same samples were subjected to FTIR ATR measurements. Data from offline reference assays and FTIR ATR infrared spectroscopic information responses were used to construct chemometric models by using PLS multivariate data analysis, and the models were cross-validated to assess their accuracy.

Protein A purified, in-house generated-harvest samples of the antibody drug candidate-X was used for this study. The monoclonal antibody used was of the IgG4 subclass and was expressed in a Chinese Hamster Ovary (CHO) mammalian expression system. The harvest samples (26 samples) were obtained from different culturing days from an alternating tangential flow perfusion bioreactor. The harvest was purified using a 0.66 cm×20 cm I.D. (6.8 mL) Protein A column packed with MabSelect SuRe LX resin using an AKTA Explorer system (available from GE Healthcare Life Sciences, Pittsburgh, PA).

A Bruker MATRIX-MF® FTIR (Bruker Optics, Billerica, MA) spectrometer equipped with an IN350T® diamond ATR (attenuated total refection) fiber optic probe and MCT (Mercury Cadmium Telluride) sensor was used for at-line measurement of samples. About 50 mL of each sample was placed on the ATR diamond crystal and spectra were measured in the wavenumber range from 400 $cm^{-1}$ to 4000 $cm^{-1}$ (scanning velocity 10 kHz, resolution 2 $cm^{-1}$, and 32 scans per run) using Bruker OPUS acquisition software (available from Bruker Optics, Billerica, MA). A reference spectrum was first recorded using a blank ATR cell on built on probe. Single-beam spectra of all samples were obtained and divided against the background spectrum of air to present the spectra in absorbance units.

The infrared vibrational information was pre-processed and chemometric partial least-squares (PLS) models for each attribute of interest were constructed by using MATLAB computation software (available from MathWorks, Natick, MA) and unscrambler camo software (CAMO Software Inc, 33300 Egypt Lane, Magnolia, TX). During pre-processing, FTIR spectra were first offset using the average absorbance values between 800-1800 $cm^{-1}$ followed by baseline correction and area normalization. Several pre-processing methods such as Linear Offset Subtraction, Straight Line Subtraction, Vector Normalization, Min-max Normalization, Multiplicative Scatter Correction, First Derivative, and Second Derivative were evaluated to improve root mean square error of cross-validation (RM-SECV) and coefficient of determination ($R^2$) of the PLS models. Offline chromatography/ELISA-based reference measurements of each attribute were correlated with pre-processed FTIR ATR spectral data in constructing PLS models.

To ensure validation of the calibration models, a cross-validation method was applied on 20 Protein A purified samples, where each FTIR ATR spectrum of the sample was validated using k-fold cross-validation in which the data set was divided into k subsets, and the k-fold model was trained and tested. Each time, one of the k subsets was used as the test set and the other k−1 subsets were pooled to form a training set. The average errors across all k trials were calculated. The wave number (or frequency) range that corresponded to each attribute value was optimized to achieve the best multivariate statistics.

Samples were also tested for antibody concentration, aggregation, charge variant distribution and host cell protein (HCP) content using offline chromatography and ELISA assays to generate reference values. The antibody concentration was measured by Protein A chromatography using a 0.21×3 cm I.D. (0.1 mL) POROS Protein A ID cartridge (available from Applied Biosystems, Foster City, CA) on an Agilent 1100 HPLC system (available from Agilent Technologies, Santa Clara, CA) followed by UV measurements of the eluates at 280 nm. The percentages of aggregated forms of the antibody in the samples were analyzed by size exclusion chromatography (SEC) using a 0.78×30 cm I.D. TSKgel G3000SWxL analytical SEC column equipped with a 0.60×4 cm I.D. TSKgel G3000SWxL guard column (available from Tosoh Bioscience, King of Prussia, PA) on the Agilent 1100 HPLC system. A 40 mM sodium phosphate elution buffer in 150 mM sodium chloride was used in isocratic mode followed by UV absorbance at 280 nm using a photodiode array detector. The HCP content of the samples was measured using a Chinese Hamster Ovary HCP ELISA kit from Cygnus technologies (available from Wrentham, MA) according to the manufacturer's manual. Samples were prepared in three dilutions followed by multiple measurements of each.

Charge variant distributions of the antibody in the samples were analyzed by capillary isoelectric focusing (cIEF) using iCE3™ system (available from ProteinSimple, San Jose, CA). Each sample was prepared in methyl celluose carrier ampholytes and was allowed to separate charge variants (Acidic and basic species) on the basis of their pI under electrolytic conditions. The in-built whole-column UV detector of the iCE3™ system was used to acquire relative distribution of charge variants.

In the infrared spectrum of protein molecule, the chemical structure of the molecule is the dominating effect that determines the observed vibrational frequencies via the strengths of the vibrating bonds and the masses of the vibrating atoms. However, it can be difficult to unambiguously determine the chemical structure of a protein based purely on the infrared spectrum due to the many overlapping bands that are typically present in the spectrum.

In spite of this, changes in the chemical structure of the molecule can often be detected based on changes in the observed spectral bands. One such example is the detection of a change in the protonation state of protein side chains, which is often essential for protein function. The protonation state of many protein side chains is reflected in the infrared spectrum of the proteins, and can often be reliably deduced from infrared spectral information.

Figure 12:
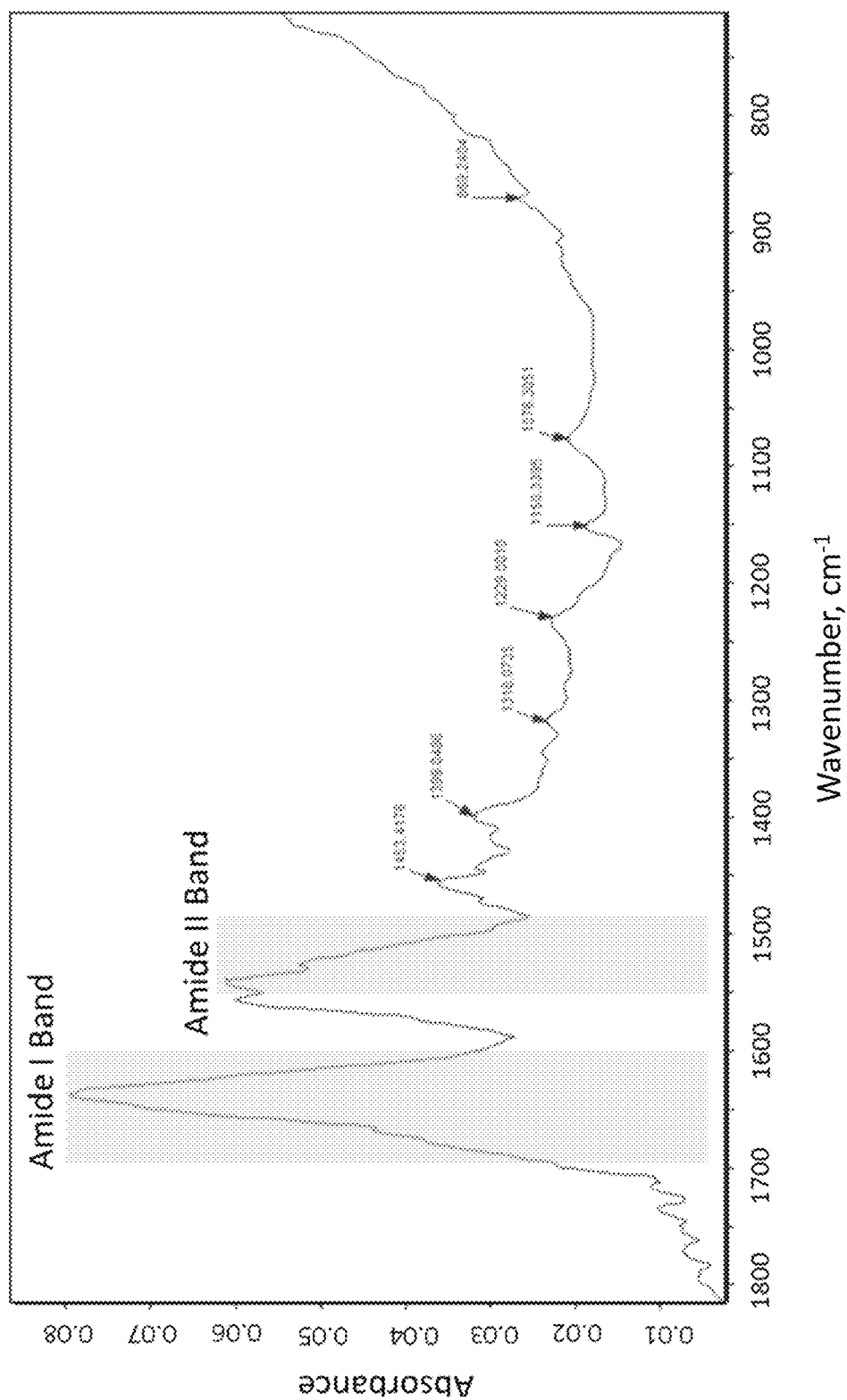
FIG. 12 is a graph showing a Fourier-transform infrared (FTIR) spectrum of a Protein A purified-antibody sample.

The FTIR ATR spectrum of a Protein A purified-antibody sample is shown in FIG. 12, where Amide I (1600-1690 $cm^{-1}$) and Amide II (1480-1575 $cm^{-1}$) characteristic bands are clearly recognizable. The Amide I band, which is due to C=O stretch vibration of the peptide backbone, is sensitive to α-helix, β-sheet, turn, and unordered conformations of the protein and their hydrogen bonding environment. Amide II originates from the N—H bending and C—N stretching vibrations and it is conformation sensitive.

In some circumstances, the Amide II band corresponds to an out-of-phase combination of the NH in-plane bending mode and the CN stretching mode with smaller contributions from the CO in-plane bending mode and the CC and NC stretching modes. In proteins, the Amide II band is typically nearly unaffected by side chain vibrations, but the correlation between protein secondary structure and frequency is less straightforward than for the Amide I band, which helps in correlating byproducts of the protein and provides valuable structural information and secondary structure predictions for the protein.

The Amide III band between 1300-1400 $cm^{-1}$ is due to N—H bend in-plane and C—N stretch. Amide IV bands are very complex bands resulting from mixtures of several coordinate displacements mostly arising at 625-725 $cm^{-1}$ due to the O=C—N deformation. The strength of hydrogen bonding in the secondary structure and coupling between different transitions dipoles of the peptide influence the absorption frequency in this region, and can be used to quantify the protein from experimental spectroscopic data.

In a biological sample, each conformational entity contributes to a molecule's FTIR ATR spectrum. Amide I band contours are complex composites consisting of several overlapping component bands that represent different structural elements such as alpha helices, beta sheets, turns, and non-ordered or irregular structures.

To extract compositional structural information encoded in those FTIR bands, FTIR spectroscopic information in frequency ranges from 1100 to 1595 $cm^{-1}$ and 1600 to 1700 $cm^{-1}$ was used to compute a PLS calibration using a second derivative-mean centered FTIR ATR spectra, with exclusion of the absorbance arising from buffer components and water. A PLS model was constructed using a k-fold cross-validation method with 20 Protein A purified samples of antibody drug candidate-X. Overtraining of the model was also analyzed and the model robustness was evaluated.

Figure 13:
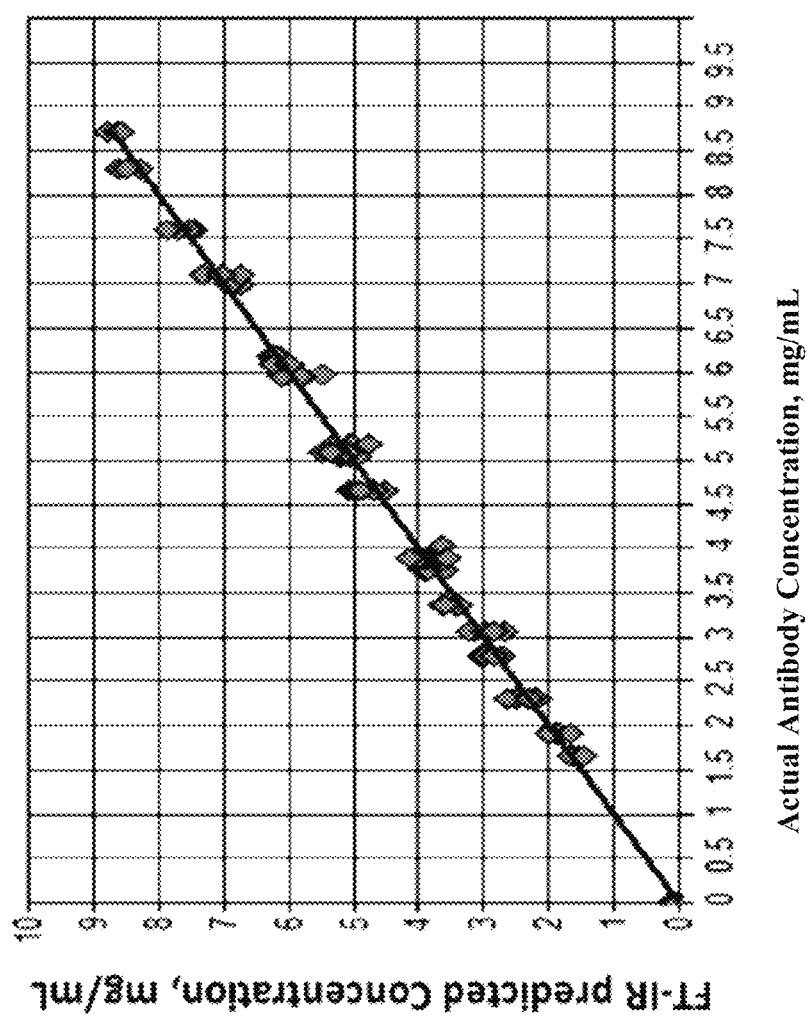
FIG. 13 is a graph showing predicted antibody concentration values calculated from a partial least-squares (PLS) model for antibody concentration, and corresponding measured antibody concentration values.

FIG. 13 is a graph showing predicted antibody concentration values calculated from the PLS model for antibody concentration, and corresponding measured antibody concentration values. The PLS model demonstrated excellent correlation between FTIR ATR predicted values and offline chromatography-based reference values. The correlation coefficient $R^2$ was 0.99 and the root mean square error of cross-validation (RMSECV) was 0.55. The accuracy of the model was evaluated by predicting the antibody concentration of 6 unknown samples using the developed calibration model. Results for the unknown samples U-1 to U-6 are shown in the table of FIG. 17.

Aggregation phenomena where proteins are mis-folded can lead to shifting of the key amide peaks in the FTIR ATR spectrum. As a result, a band-narrowing Fourier self-deconvolution technique was used to estimate the FTIR range and positions of discrete subcomponent absorption bands. The Fourier self-deconvolution decreases band widths, allowing separation of overlapping component bands using Gaussian functions.

Figure 14A:
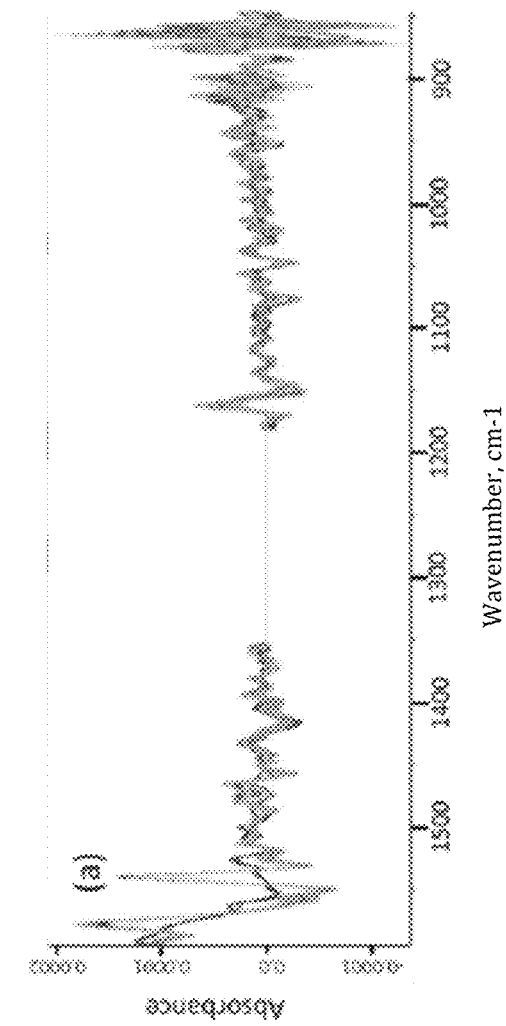
FIG. 14A is a graph showing an example of Fourier self-deconvolved FTIR infrared spectra of Protein A purified samples.

The vibrational frequency of an aggregated protein falls around 1620-1625 $cm^{-1}$ due to the distinct hydrophobic environment, and often shows frequency shift of Amide II (~1540 $cm^{-1}$). Therefore, the FTIR regions from 1393-1554 $cm^{-1}$ and 1600-1635 $cm^{-1}$ were selected to develop a calibration model. In addition, the FTIR region from 1180-844 $cm^{-1}$ was selected to improve the prediction accuracy due to the C—O—H vibrations of proteins. FIG. 14A shows an example of the Fourier self-deconvolved FTIR spectra of Protein A purified samples.

Figure 14B:
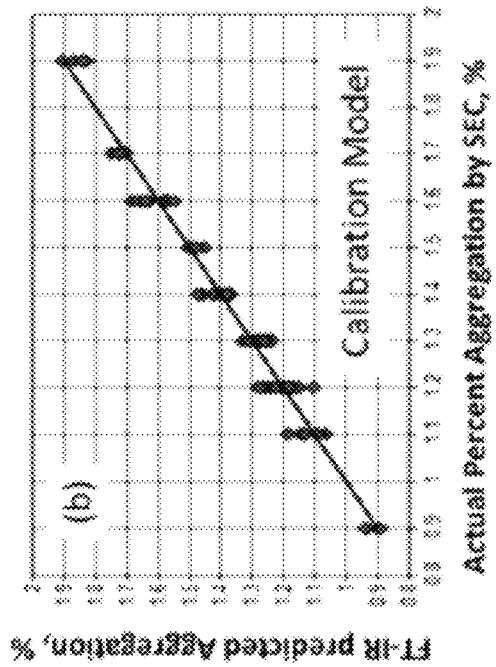
FIG. 14B is a graph showing a PLS calibration model developed for aggregation values for a sample, and measured aggregation values for the sample.

FIG. 14B is a graph showing the PLS calibration model developed for aggregation (solid line) and measured aggregation values (dots). The PLS calibration model demonstrated excellent correlation between FTIR predicted aggregation values (%) with reference SEC values. The RMSECV, $R^2$ and relative percent difference (RDP) values were 0.04, 0.97 and 5.8 respectively.

One of the challenges in constructing robust chemometric models for low concentration species such as HCPs is the influence from polyelectrolytes in the medium. It is known that peaks appearing at approximately 1,390 $cm^{-1}$ and 1005-110 $cm^{-1}$ can be assigned to polyelectrolytes. FIG. 15A shows a set of mean-centered, baseline-corrected, and area-averaged second derivative FTIR ATR spectra used for the construction of a PLS model for HCPs.

To develop the PLS model for HCP quantitative determination, mid-IR region frequency ranges from 1500-1600 $cm^{-1}$, 1600-1680 $cm^{-1}$, 1489-1414 $cm^{-1}$, and 1174-1286 $cm^{-1}$ were used. All of the spectra were mean-centered, baseline-corrected, and area-averaged, as shown in FIG. 15A.

Figure 15B:
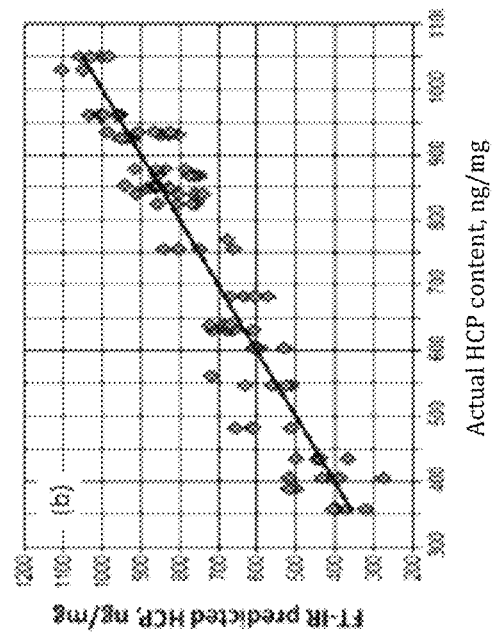
FIG. 15B is a graph showing a PLS model for HCP content of a sample determined from the spectra in FIG. 15A, and measured HCP values for the sample.
Figure 15A:
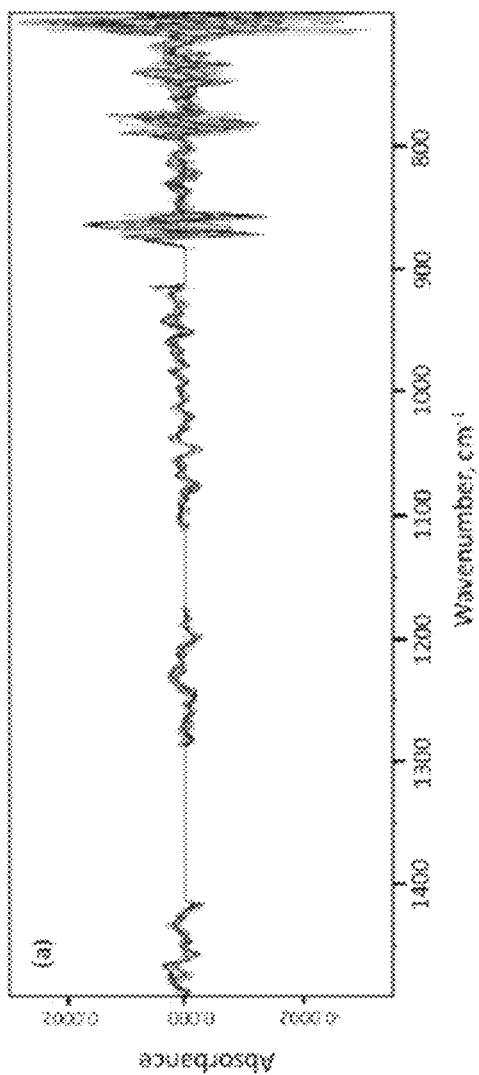
FIG. 15A is a graph showing a set of spectra used to construct a PLS model for host cell protein (HCP) content of a sample.

FIG. 15B is a graph showing the model for HCP quantitative determination (solid line) and measured HCP values (dots). A fairly good correlation is observed, with $R^2$=0.89, RMSECV=71.1, and RPD=3.05.

To evaluate PLS models for determining the charge variant distribution, pre-processed FTIR ATR spectra of the samples were subjected to k-fold cross-validation using 20 samples for pre-Main (acidic), Main, and post-Main (basic) species to construct three separate models, respectively. Overtraining and robustness of the models were evaluated. The analysis of charge variants depends largely on C-terminal lysine modifications, which lead to spectrum pattern shift mostly in the fingerprint region from 1000 to 1850 $cm^{-1}$. Accordingly, mean-centered spectra subjected to multiple scatter corrections and second derivative analysis from 1118 $cm^{-1}$ to 1500 $cm^{-1}$ were used for the construction of the PLS model for the Main peak, which is shown (solid line) in FIG. 16B. PLS statistics for the Main peak model include $R^2$ of 0.99, RMSECV of 0.00, 1 and RPD of 12.4.

For the pre-Main analysis, the FTIR region from 1120 $cm^{-1}$ to 1470 $cm^{-1}$ yielded the best PLS calibration model, using PLS rank up to 10. The model is shown in FIG. 16A. The RMSECV, $R^2$, and RPD values were 0.00125, 0.9937, and 12.6 respectively.

Figure 16C:
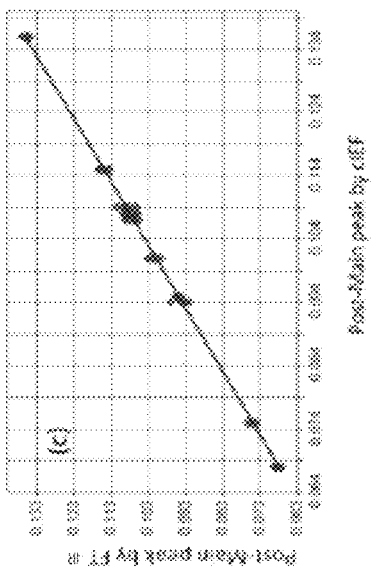
FIGS. 16A-16C are graphs showing three different PLS models for charge variant distribution values of a sample.
Figure 16B:
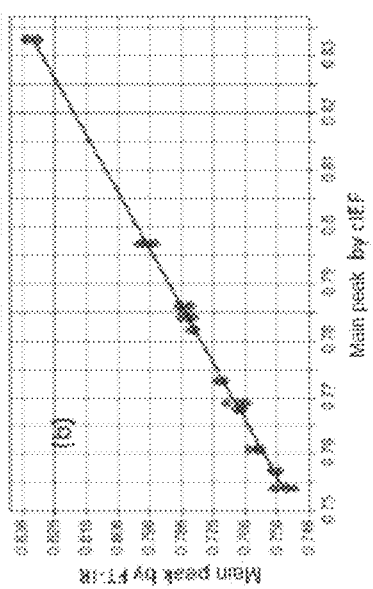
Figure 16A:
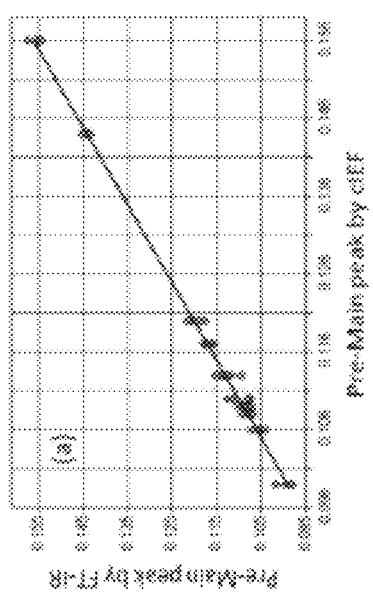
Figures 18A, 18B, 18C, 18D:
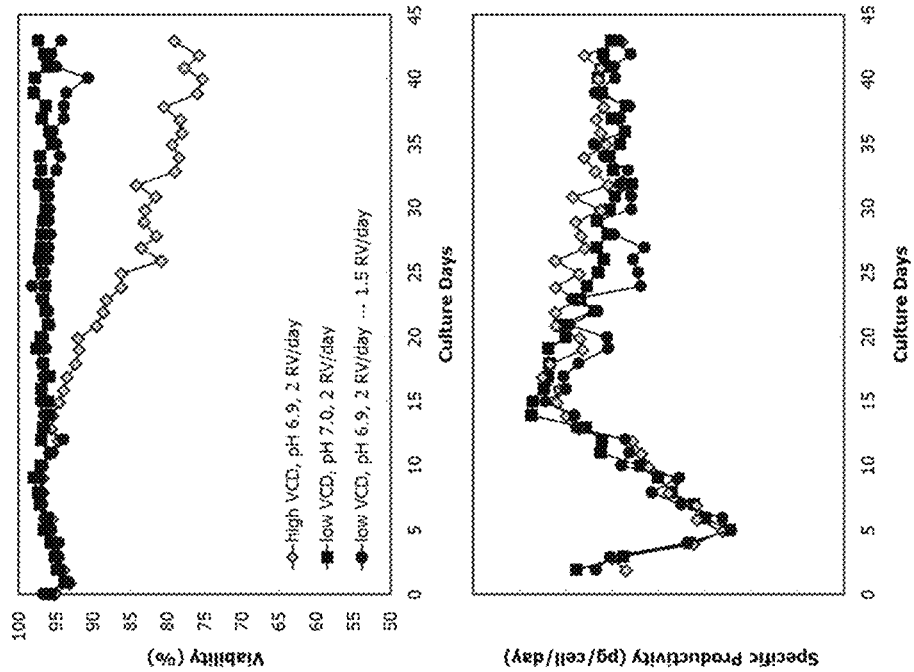
FIGS. 18A-18D are graphs showing measurements of viable cell density, cell viability, harvest titer, and specific productivity for a perfusion bioreactor.

For the post-Main analysis, the FTIR region from 1187 $cm^{-1}$ to 1839 $cm^{-1}$ was used to construct the PLS model, which is shown on the graph of FIG. 16C. An excellent correlation with measured values from the reference cIEF method was achieved. The RMSECV, $R^2$ and RPD values were 0.00118, 99.59, and 15.7. The accuracy of the models was also evaluated by predicting the charge variant distribution of 6 unknown samples, U-1 to U-6, the results of which are shown in FIG. 17.

To evaluate the effectiveness of using in-line infrared spectral measurements and chemometric models to accurately determine values of bioreactor medium components and conditions, the methods disclosed herein were applied to the measurement of glucose concentration, glutamine concentration, IgG concentration, lactate concentration, ammonia concentration, and osmolarity. Specifically, in-line ATR infrared spectral measurements were performed on the reactor medium, and validated chemometric models for each of these quantities were used to predict values for each of the quantities from the infrared spectral measurements. To determine the accuracy of the infrared-derived values, the reactor medium was also manually sampled and values of each of the quantities was determined via individual analysis.

FIGS. 21A-21F are graphs showing "true" values (diamond markers) and predicted (or infrared-derived) values (solid line) of glucose concentration (FIG. 21A), glutamine concentration (FIG. 21B), IgG concentration (FIG. 21C), lactate concentration (FIG. 21D), ammonium ion concentration (FIG. 21E), and osmolarity (FIG. 21F) for the bioreactor medium. Excellent agreement between the true and predicted values was achieved for each measured quantity.

Figure 22A:
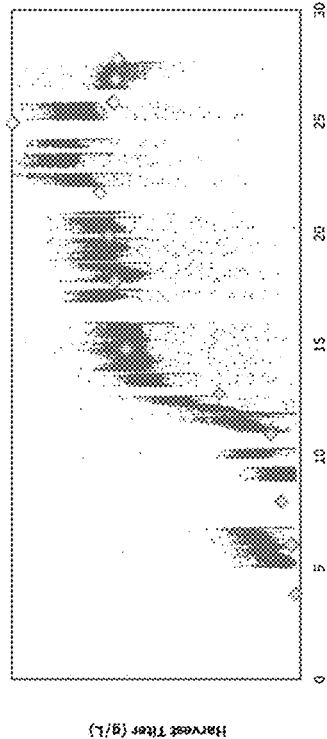
FIGS. 22A-22D are graphs showing multiple values of glucose concentration, harvest titer, lactate concentration, and ammonium ion concentration determined for a bioreactor medium from infrared spectral information.
Figure 22B:
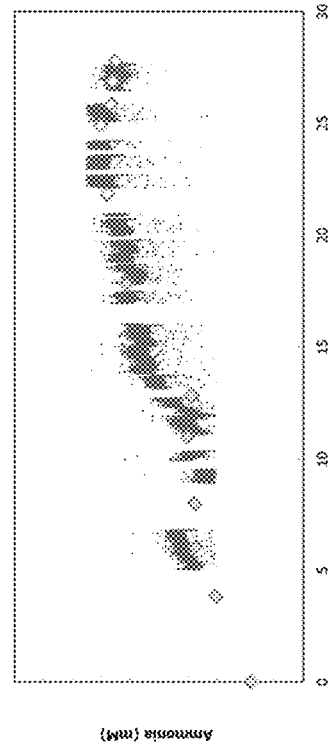
Figure 22C:
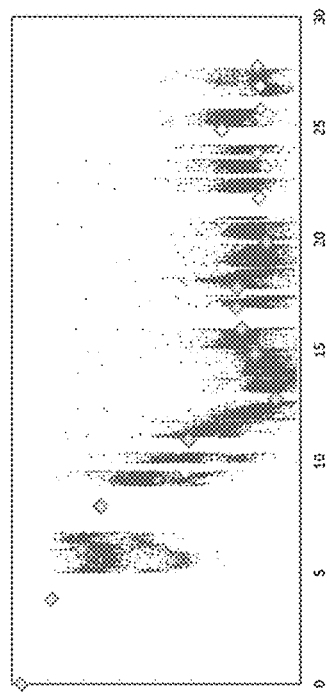
Figure 22D:
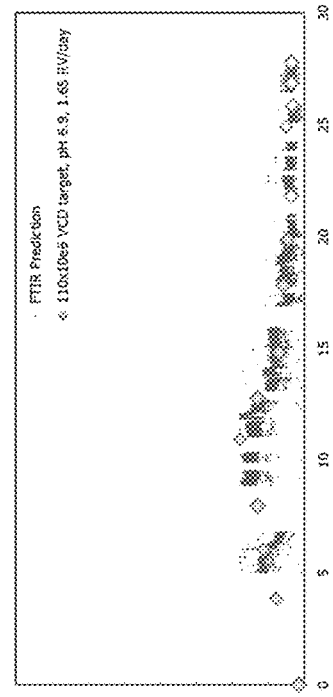

FIGS. 22A-22D are graphs showing true (diamond markers) and predicted (dot markers) values of glucose concentration (FIG. 22A), harvest titer (FIG. 22B), lactate concentration (FIG. 22C), and ammonium ion concentration (FIG. 22D). For each true value, multiple predicted values were determined from multiple infrared spectral measurements, and the distribution of dot markers in FIGS. 22A-22D indicate the variability of the values predicted based in infrared spectral information. Although a relatively small number of outliers appear in each of the figures, most of the individually predicted values are in close agreement with the true values of the various quantities, and the distributions of each set of infrared-determined values is in agreement with the corresponding true value.

Figure 23A:
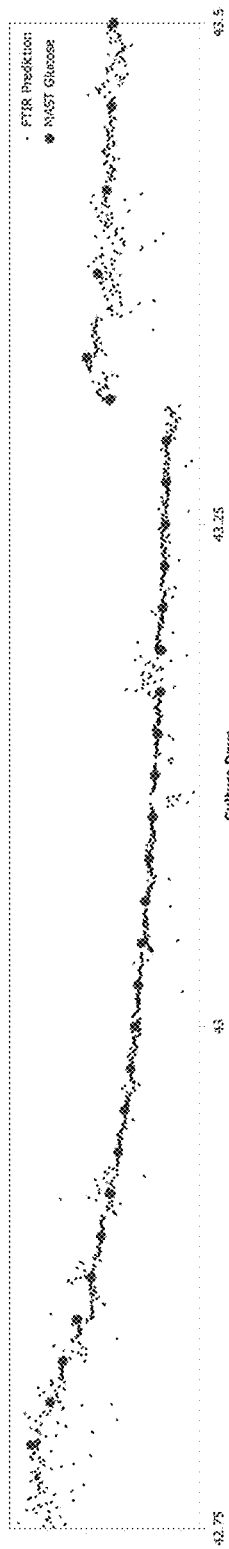
FIGS. 23A-23C are graphs showing multiple values of glucose concentration, lactate concentration, and ammonium ion concentration at later stages of a bioreactor culture medium, determined from infrared spectral information.
Figure 23B:
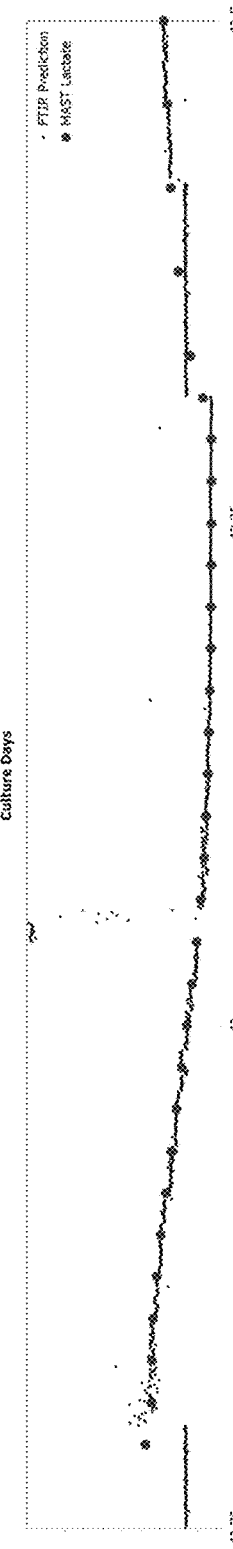
Figure 23C:
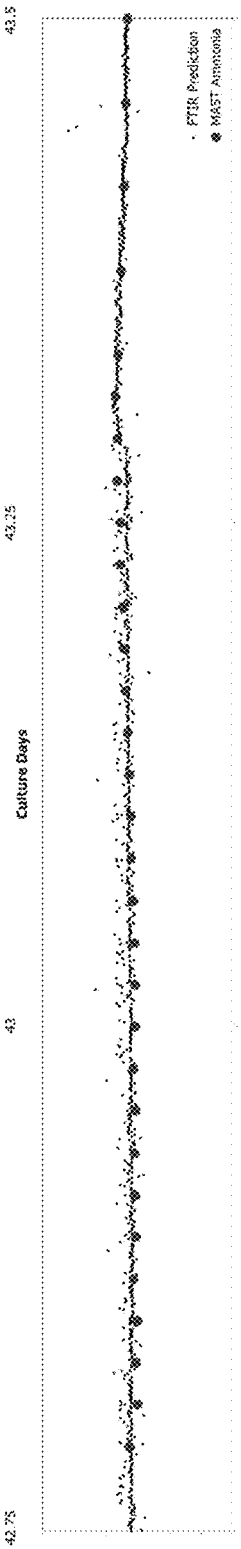

FIGS. 23A-23C are graphs showing true (large dots) and predicted (i.e., infrared-determined, small dots) values of glucose concentration (FIG. 23A), lactate concentration (FIG. 23B), and ammonium ion concentration (FIG. 23C) at later stages of a bioreactor culture medium, in days 42 and 43. As is evident from the graphs, the infrared-determined values of these quantities continue to agree well with the true values, demonstrating that chemometrics-based methods that rely on infrared spectral information to determine values of multiple different medium component-related quantities remain highly accurate, even as the cell culture and medium continue to yield products after a relatively long time.

What is claimed is:

1. A biological manufacturing system, comprising:
a radiation source configured to generate radiation;
a detection apparatus comprising:
an optical fiber comprising two fiber cores in a common cladding;
an optical element integrated into an end of the optical fiber so that at least a portion of the optical element is located within the common cladding, and positioned so that the generated radiation propagating through a first fiber core of the two fiber cores is incident on a first side of a surface of the optical element, wherein a flowing solution is located on a second side of the surface of the optical element opposite the first side, and radiation that undergoes total internal reflection from the surface of the optical element and does not propagate through the flowing solution is coupled into a second fiber core of the two fiber cores; and
a detector positioned to receive the radiation that undergoes total internal reflection from the second fiber core; and
a system controller connected to the detection apparatus, and configured to:
receive a measurement signal from the detection apparatus corresponding to an infrared vibrational spectrum of the solution;
analyze the infrared vibrational spectrum using a first chemometrics model to determine value of a first quality attribute associated with the solution;
analyze the infrared vibrational spectrum using a second chemometrics model to determine a value of a second quality attribute associated with the solution; and
adjust at least one parameter of the biological manufacturing system based on at least one of the values of the first and second quality attributes.

2. The system of claim 1, wherein the biological manufacturing system is configured to produce the solution, and the flowing solution is derived from a bioreactor or the flowing solution is received from a purification unit of the biological manufacturing system.

3. The system of claim 1, wherein the flowing solution comprises a biological product comprising at least one of a protein-based therapeutic substance, a nucleic acid-based drug substance, and a gene therapy drug substance.

4. The system of claim 1, wherein the first and second quality attributes are each independently selected from the group consisting of product quality attributes, product-related impurities, and process-related impurities, for a biological product produced by the biological manufacturing system.

5. The system of claim 2, further comprising a flow cell positioned to receive the solution derived from a bioreactor of the biological manufacturing system, wherein the optical element is further integrated with a portion of the flow cell.

6. The system of claim 1, wherein the first chemometrics model comprises a first set of at least three principal vibrational components correlated with the first quality attribute.

7. The system of claim 6, wherein the second chemometrics model comprises a second set of at least three principal vibrational components correlated with the second quality attribute, and wherein the first and second sets of principal vibrational components have no members in common.

8. The system of claim 1, wherein adjusting the at least one parameter of the biological manufacturing system comprises transmitting a signal comprising instructions to adjust a pH of a solution in a bioreactor of the biological manufacturing system.

9. The system of claim 1, wherein adjusting the at least one parameter of the biological manufacturing system comprises adjusting a concentration of a species in a bioreactor of the biological manufacturing system, wherein the species comprises at least one member selected from the group consisting of lactate ions, ammonium ions, glucose, and glutamine.

10. The system of claim 1, wherein adjusting the at least one parameter of the biological manufacturing system comprises adjusting a cell density in a bioreactor of the biological manufacturing system.

11. The system of claim 1, wherein the first and second fiber cores are coupled to different surfaces of the optical element.

12. The system of claim 1, wherein the optical element comprises an incident surface through the generated radiation enters the optical element from the first fiber core, and wherein the incident surface is oriented non-orthogonally with respect to an axis of the optical fiber.

13. A biological manufacturing system, comprising:
a first purification unit configured to purify a solution comprising a biological product;
a second purification unit configured to receive the solution from the first purification unit;
a flow cell positioned so that the solution passes through the flow cell between the first and second purification units;
a radiation source configured to generate radiation;
a detection apparatus comprising:
an optical fiber comprising two fiber cores in a common cladding;
an optical element integrated into an end of the optical fiber so that at least a portion of the optical element is located within the common cladding, and positioned so that the generated radiation propagating through a first fiber core of the two fiber cores is incident on a first side of a surface of the optical element, wherein the solution is located on a second side of the surface of the optical element opposite the first side, and radiation that undergoes total internal reflection from the surface of the optical element and does not propagate through the flowing solution is coupled into a second fiber core of the two fiber cores; and
a detector positioned to receive the radiation that undergoes total internal reflection from the second fiber core; and
a system controller connected to the detection apparatus, and configured to:
receive a measurement signal from the detection apparatus corresponding to an infrared vibrational spectrum of the solution;
analyze the infrared vibrational spectrum using a first chemometrics model to determine value of a first quality attribute associated with the solution;
analyze the infrared vibrational spectrum using a second chemometrics model to determine a value of a second quality attribute associated with the solution; and
adjust at least one parameter of the first purification unit based on at least one of the values of the first and second quality attributes.

14. The system of claim 13, wherein the biological product comprises at least one of a protein-based therapeutic substance, a nucleic acid-based drug substance, and a gene therapy drug substance.

15. The system of claim 13, wherein the first and second quality attributes are each independently selected from the group consisting of product quality attributes, product-related impurities, and process-related impurities, for a biological product produced by the biological manufacturing system.

16. The system of claim 13, wherein the optical element is further integrated with a portion of the flow cell.

17. The system of claim 13, wherein the first chemometrics model comprises a first set of at least three principal vibrational components correlated with the first quality attribute, and the controller is configured to analyze the vibrational spectrum using the first chemometrics model by calculating the first quality attribute value based on the first set of principal vibrational components.

18. The system of claim 17, wherein the second chemometrics model comprises a second set of at least three principal vibrational components correlated with the second quality attribute, and wherein the first and second sets of principal vibrational components have no members in common.

19. The system of claim 13, wherein adjusting the at least one parameter comprises selectively directing one eluent stream from among multiple eluent streams into the second purification unit from the first purification unit.

20. The system of claim 13, wherein adjusting the at least one parameter comprises at least one member selected from the group consisting of adjusting a pH of the solution in the first purification unit, and adjusting a buffer composition of the solution in the first purification unit.

21. The system of claim 13, wherein adjusting the least one parameter comprises adjusting a retention time of the solution in the first purification unit.

22. The system of claim 13, wherein the first and second fiber cores are coupled to different surfaces of the optical element.

23. The system of claim 13, wherein the optical element comprises an incident surface through the generated radiation enters the optical element from the first fiber core, and wherein the incident surface is oriented non-orthogonally with respect to an axis of the optical fiber.

* * * * *